US011393251B2

(12) United States Patent
Tonsen et al.

(10) Patent No.: US 11,393,251 B2
(45) Date of Patent: Jul. 19, 2022

(54) DEVICES, SYSTEMS AND METHODS FOR PREDICTING GAZE-RELATED PARAMETERS

(71) Applicant: Pupil Labs GmbH, Berlin (DE)

(72) Inventors: Marc Tonsen, Berlin (DE); Kai Dierkes, Berlin (DE); Moritz Kassner, Berlin (DE); Bernhard Petersch, Berlin (DE)

(73) Assignee: Pupil Labs GmbH, Berlin (DE)

( * ) Notice: Subject to any disclaimer, the term of this patent is extended or adjusted under 35 U.S.C. 154(b) by 0 days.

(21) Appl. No.: 16/967,323

(22) PCT Filed: Feb. 9, 2018

(86) PCT No.: PCT/EP2018/053294
§ 371 (c)(1),
(2) Date: Aug. 4, 2020

(87) PCT Pub. No.: WO2019/154510
PCT Pub. Date: Aug. 15, 2019

(65) Prior Publication Data
US 2020/0364453 A1    Nov. 19, 2020

(51) Int. Cl.
*G06V 40/19* (2022.01)
*G06T 7/73* (2017.01)
(Continued)

(52) U.S. Cl.
CPC ............... *G06V 40/19* (2022.01); *G06T 7/73* (2017.01); *G06V 10/82* (2022.01); *G06V 40/18* (2022.01);
(Continued)

(58) Field of Classification Search
CPC ............. G06K 9/00604; G06K 9/6267; G06K 9/00597; G06T 7/73; G06T 2207/20084;
(Continued)

(56) References Cited

U.S. PATENT DOCUMENTS 4,852,988 A    8/1989 Velez et al.
6,351,273 B1   2/2002 Lemelson et al.
(Continued)

FOREIGN PATENT DOCUMENTS

CA    2967756    10/2005
CA    2750287    11/2011
(Continued)

OTHER PUBLICATIONS

Moritz Kassner, Will Patera, Andreas Bulling: "Pupil: An Open Source Platform for Pervasive Eye Tracking and Mobile Gaze-based Interaction", Proceedings of the 2014 ACM International Joint Conference on Pervasive and Ubiquitous Computing: Adjunct Publication, pp. 1151-1160, ACM Sep. 13-17, 2014.
(Continued)

*Primary Examiner* — Tat C Chio
(74) *Attorney, Agent, or Firm* — Dicke, Billig & Czaja, PLLC

(57) ABSTRACT

A method for detecting one or more gaze-related parameters of a user is disclosed. In one example, the method includes creating a left image of at least a portion of a left eye of the user using a first camera of a head-wearable device worn by the user, and creating a right image of at least a portion of a right eye of the user using a second camera of the head-wearable device. The left and right images are fed together as an input into a convolutional neural network. One or more gaze-related parameters are obtained from the convolutional neural network as a result of the left and right images input.

20 Claims, 6 Drawing Sheets

(51) Int. Cl.
*G06V 10/82* (2022.01)
*G06V 40/18* (2022.01)
*G06N 3/04* (2006.01)

(52) U.S. Cl.
CPC ...... *G06N 3/04* (2013.01); *G06T 2207/20084* (2013.01); *G06T 2207/30201* (2013.01)

(58) Field of Classification Search
CPC ............ G06T 2207/30201; G06N 3/04; A61B 5/163; A61B 5/18; A61B 3/113
See application file for complete search history.

(56) References Cited

U.S. PATENT DOCUMENTS

| | | | |
|---|---|---|---|
| 6,943,754 B2 | 9/2005 | Aughey et al. |
| 7,488,294 B2 | 2/2009 | Torch |
| 7,815,311 B2 | 10/2010 | Johns et al. |
| 8,091,546 B2 | 1/2012 | Mantell |
| 8,342,687 B2 | 1/2013 | Blixt et al. |
| 8,594,374 B1 | 11/2013 | Bozarth |
| 8,624,994 B2 | 1/2014 | Kaneda et al. |
| 8,830,142 B1 | 1/2014 | Kim et al. |
| 8,752,963 B2 | 6/2014 | McCulloch et al. |
| 8,761,459 B2 | 6/2014 | Kaneda et al. |
| 8,836,768 B1 | 9/2014 | Rafii et al. |
| 8,929,589 B2 | 1/2015 | Publicover et al. |
| 8,982,046 B2 | 3/2015 | Edwards et al. |
| 9,185,352 B1 | 11/2015 | Jacques |
| 9,189,095 B2 | 11/2015 | Eden et al. |
| 9,207,760 B1 | 12/2015 | Wu et al. |
| 9,253,442 B1* | 2/2016 | Pauli .................. H04N 7/15 |
| 9,380,287 B2 | 6/2016 | Nistico et al. |
| 9,405,365 B2 | 8/2016 | Publicover et al. |
| 9,451,166 B1 | 9/2016 | Ribardo, Jr. et al. |
| 9,501,683 B1 | 11/2016 | Hatstat et al. |
| 9,529,442 B2 | 12/2016 | Cho et al. |
| 9,600,069 B2 | 3/2017 | Publicover et al. |
| 9,668,648 B2 | 6/2017 | Pfleger et al. |
| 9,672,416 B2 | 6/2017 | Zhang et al. |
| 9,693,684 B2 | 7/2017 | Lopez et al. |
| 9,727,136 B2 | 8/2017 | Willairat et al. |
| 9,737,209 B2 | 8/2017 | Gramatikov et al. |
| 9,785,233 B2 | 10/2017 | San Agustin Lopez et al. |
| 9,801,539 B2 | 10/2017 | Kerr et al. |
| 9,811,158 B2 | 11/2017 | Hennessey et al. |
| 9,851,091 B2 | 12/2017 | Im et al. |
| 9,936,195 B2 | 4/2018 | Horesh |
| 9,958,941 B2 | 5/2018 | Gustafsson et al. |
| 9,961,307 B1 | 5/2018 | Weinblatt |
| 9,977,960 B2 | 5/2018 | Gustafsson et al. |
| 10,016,131 B2 | 7/2018 | Liu et al. |
| 10,048,749 B2 | 8/2018 | Miao et al. |
| 10,114,459 B2 | 10/2018 | Algotsson et al. |
| 10,157,313 B1 | 12/2018 | Zhang et al. |
| 10,229,511 B2 | 3/2019 | Meier |
| 10,285,589 B2 | 5/2019 | Hart et al. |
| 10,303,250 B2 | 5/2019 | Jeong |
| 10,307,053 B2 | 6/2019 | Fayolle |
| 10,416,764 B2 | 9/2019 | Wanner et al. |
| 10,438,373 B2 | 10/2019 | Wang et al. |
| 10,452,137 B2 | 10/2019 | Noda et al. |
| 10,488,668 B2 | 11/2019 | Cazalet |
| 10,489,680 B2* | 11/2019 | Aliabadi ............... G06N 3/0454 |
| 10,496,160 B2 | 12/2019 | Lu et al. |
| 10,514,542 B2 | 12/2019 | Erinjippurath et al. |
| 10,546,193 B2 | 1/2020 | Schmidt et al. |
| 10,546,194 B2 | 1/2020 | Tsurumi |
| 10,634,934 B2 | 4/2020 | Chene et al. |
| 10,698,205 B2 | 6/2020 | Huang |
| 10,909,711 B2 | 2/2021 | Schroeder et al. |
| 10,976,813 B2 | 4/2021 | Nistico et al. |
| 11,017,558 B2 | 5/2021 | Noble et al. |
| 11,023,038 B2 | 6/2021 | Yasuda et al. |
| 11,033,204 B2 | 6/2021 | Massonneau et al. |

| | | | |
|---|---|---|---|
| 2003/0184868 A1 | 10/2003 | Geist |
| 2004/0174496 A1 | 9/2004 | Ji et al. |
| 2005/0034287 A1 | 2/2005 | Xie |
| 2005/0225723 A1 | 10/2005 | Pilu |
| 2006/0240005 A1 | 10/2006 | Velardi |
| 2006/0279692 A1 | 12/2006 | Bruck |
| 2007/0066916 A1 | 3/2007 | Lemos |
| 2009/0190026 A1 | 7/2009 | Chen |
| 2010/0045933 A1 | 2/2010 | Eberl et al. |
| 2010/0053555 A1 | 3/2010 | Enriquez et al. |
| 2010/0220288 A1 | 9/2010 | Cleveland |
| 2012/0212593 A1 | 8/2012 | Na'aman et al. |
| 2012/0290401 A1 | 11/2012 | Neven |
| 2012/0293773 A1 | 11/2012 | Publicover et al. |
| 2013/0050070 A1 | 2/2013 | Lewis et al. |
| 2013/0066213 A1 | 3/2013 | Wellington |
| 2013/0069883 A1 | 3/2013 | Oga |
| 2013/0083976 A1 | 4/2013 | Ragland |
| 2013/0114043 A1 | 5/2013 | Balan et al. |
| 2013/0120224 A1 | 5/2013 | Cajigas et al. |
| 2013/0207887 A1 | 8/2013 | Raffle et al. |
| 2013/0222213 A1 | 8/2013 | Abdollahi et al. |
| 2013/0318776 A1 | 12/2013 | Jacobs et al. |
| 2013/0321925 A1 | 12/2013 | Jacobs et al. |
| 2014/0022371 A1 | 1/2014 | Huang et al. |
| 2014/0043581 A1 | 2/2014 | Chen |
| 2014/0049452 A1 | 2/2014 | Maltz |
| 2014/0055591 A1 | 2/2014 | Katz |
| 2014/0055746 A1 | 2/2014 | Nistico et al. |
| 2014/0055747 A1* | 2/2014 | Nistico ................. A61B 3/14 351/206 |
| 2014/0152558 A1 | 6/2014 | Salter et al. |
| 2014/0156219 A1 | 6/2014 | Soubra et al. |
| 2014/0191927 A1 | 7/2014 | Cho |
| 2014/0218281 A1 | 8/2014 | Amayeh et al. |
| 2014/0226131 A1 | 8/2014 | Lopez et al. |
| 2014/0247232 A1 | 9/2014 | George-Svahn et al. |
| 2014/0285404 A1 | 9/2014 | Takano et al. |
| 2014/0354953 A1 | 12/2014 | Chen et al. |
| 2015/0070470 A1 | 3/2015 | McMurrough |
| 2015/0085251 A1 | 3/2015 | Larsen |
| 2015/0169050 A1 | 6/2015 | Publicover et al. |
| 2015/0181100 A1 | 6/2015 | Publicover et al. |
| 2015/0302585 A1 | 10/2015 | VanBlon et al. |
| 2015/0310263 A1 | 10/2015 | Zhang et al. |
| 2016/0004306 A1 | 1/2016 | Maltz |
| 2016/0005176 A1 | 1/2016 | Nguyen et al. |
| 2016/0011658 A1 | 1/2016 | Lopez et al. |
| 2016/0166190 A1 | 1/2016 | Publicover et al. |
| 2016/0109945 A1 | 4/2016 | Kempinski |
| 2016/0126675 A2 | 5/2016 | Daoura |
| 2016/0166146 A1 | 6/2016 | Sarkar |
| 2016/0187969 A1 | 6/2016 | Larsen et al. |
| 2016/0202756 A1 | 7/2016 | Wu et al. |
| 2016/0206196 A1 | 7/2016 | Pfleger et al. |
| 2016/0224110 A1 | 8/2016 | Massonneau et al. |
| 2016/0246367 A1 | 8/2016 | Tungare et al. |
| 2016/0252751 A1 | 9/2016 | Kim |
| 2016/0262608 A1 | 9/2016 | Krueger |
| 2016/0267708 A1 | 9/2016 | Nistico et al. |
| 2016/0286110 A1 | 9/2016 | Ribardo, Jr. et al. |
| 2016/0328016 A1 | 11/2016 | Andersson et al. |
| 2017/0004363 A1 | 1/2017 | Dore et al. |
| 2017/0017299 A1 | 1/2017 | Biedert et al. |
| 2017/0031437 A1 | 2/2017 | Qian et al. |
| 2017/0035293 A1 | 2/2017 | Nistico et al. |
| 2017/0038607 A1 | 2/2017 | Camara |
| 2017/0116476 A1 | 4/2017 | Publicover et al. |
| 2017/0123491 A1 | 5/2017 | Hansen |
| 2017/0136626 A1 | 5/2017 | Wang et al. |
| 2017/0176778 A1 | 6/2017 | Ushakov |
| 2017/0188823 A1 | 7/2017 | Ganesan et al. |
| 2017/0243387 A1 | 8/2017 | Li et al. |
| 2017/0276934 A1 | 9/2017 | Sarkar |
| 2017/0308734 A1 | 10/2017 | Chalom et al. |
| 2017/0332901 A1* | 11/2017 | Hwang ................. A61B 3/14 |
| 2017/0351326 A1 | 12/2017 | Aarts et al. |
| 2017/0363885 A1 | 12/2017 | Blum et al. |
| 2017/0372487 A1 | 12/2017 | Lagun et al. |

(56) References Cited

U.S. PATENT DOCUMENTS

| | | | |
|---|---|---|---|
| 2018/0018451 A1 | 1/2018 | Spizhevoy et al. | |
| 2018/0032131 A1 | 2/2018 | Yasuda et al. | |
| 2018/0059782 A1 | 3/2018 | San Agustin et al. | |
| 2018/0089834 A1 | 3/2018 | Spizhevoy et al. | |
| 2018/0095295 A1 | 4/2018 | Chene et al. | |
| 2018/0103194 A1 | 4/2018 | Tang | |
| 2018/0103903 A1 | 4/2018 | Tzvieli et al. | |
| 2018/0137358 A1 | 5/2018 | Rousseau et al. | |
| 2018/0157045 A1 | 6/2018 | Davami | |
| 2018/0157892 A1 | 6/2018 | Han et al. | |
| 2018/0180893 A1 | 6/2018 | Gupta | |
| 2018/0181809 A1 | 6/2018 | Ranjan et al. | |
| 2018/0267604 A1 | 9/2018 | Bhattacharya | |
| 2018/0286070 A1 | 10/2018 | Benedetto | |
| 2019/0005679 A1 | 1/2019 | Nie | |
| 2019/0043216 A1 | 2/2019 | Yabuuchi et al. | |
| 2019/0076015 A1 | 3/2019 | Johansson et al. | |
| 2019/0080474 A1 | 3/2019 | Lagun et al. | |
| 2019/0082170 A1 | 3/2019 | Akahori | |
| 2019/0086669 A1 | 3/2019 | Percival et al. | |
| 2019/0087973 A1 | 3/2019 | Kaehler et al. | |
| 2019/0156100 A1 | 5/2019 | Rougeaux et al. | |
| 2019/0265788 A1 | 8/2019 | Tosha et al. | |
| 2020/0183190 A1 | 6/2020 | Rousseau et al. | |
| 2020/0335065 A1 | 10/2020 | Furuta et al. | |
| 2021/0041701 A1 | 2/2021 | Kassner et al. | |
| 2021/0049410 A1 | 2/2021 | Dierkes et al. | |
| 2021/0247617 A1 | 8/2021 | Kassner et al. | |

FOREIGN PATENT DOCUMENTS

| | | | | |
|---|---|---|---|---|
| CN | 102930252 | | 2/2013 | |
| CN | 103356163 | | 10/2013 | |
| CN | 105676456 | | 6/2016 | |
| CN | 106599994 | | 4/2017 | |
| CN | 206805020 | | 12/2017 | |
| CN | 107545302 | | 1/2018 | |
| CN | 107545302 A | * | 1/2018 | ............ A61B 3/113 |
| CN | 107564062 | | 1/2018 | |
| CN | 109254420 | | 1/2019 | |
| CN | 109298533 | | 2/2019 | |
| CN | 109820524 | | 5/2019 | |
| DE | 19807902 | | 9/1999 | |
| DE | 102009049849 | | 4/2011 | |
| DE | 10 2010 018 562 | | 10/2011 | |
| DE | 10 2014 206 623 | | 10/2015 | |
| DE | 10 2016 210 288 | | 12/2017 | |
| EP | 1403680 | | 3/2004 | |
| EP | 1755441 | | 2/2007 | |
| EP | 1027627 | | 2/2009 | |
| EP | 2096577 | | 9/2009 | |
| EP | 2309307 | | 4/2011 | |
| EP | 2416280 | | 2/2012 | |
| EP | 2490155 | | 8/2012 | |
| EP | 2573650 | | 3/2013 | |
| EP | 2784632 | | 10/2014 | |
| EP | 2805671 | | 11/2014 | |
| EP | 2886041 | | 6/2015 | |
| EP | 2795888 | | 9/2015 | |
| EP | 2940555 | | 11/2015 | |
| EP | 2943835 | | 11/2015 | |
| EP | 2956844 | | 12/2015 | |
| EP | 2980628 | | 2/2016 | |
| EP | 3005030 | | 4/2016 | |
| EP | 3047883 | | 7/2016 | |
| EP | 3059629 | | 8/2016 | |
| EP | 3112922 | | 1/2017 | |
| EP | 3129849 | | 2/2017 | |
| EP | 3135464 | | 3/2017 | |
| EP | 3137938 | | 3/2017 | |
| EP | 3228238 | | 10/2017 | |
| EP | 3236338 | | 10/2017 | |
| EP | 3252566 | | 12/2017 | |
| EP | 3258308 | | 12/2017 | |
| EP | 3267295 | | 2/2018 | |
| EP | 3305176 | | 4/2018 | |
| EP | 3305179 | | 4/2018 | |
| EP | 3376163 | | 9/2018 | |
| EP | 3460785 | | 3/2019 | |
| EP | 3521911 | | 8/2019 | |
| FR | 3081565 | | 11/2019 | |
| TW | M401786 | | 4/2011 | |
| WO | 9905988 | | 2/1999 | |
| WO | 9926126 | | 5/1999 | |
| WO | 2005009466 | | 2/2005 | |
| WO | 2005094667 | | 10/2005 | |
| WO | 2007/016739 | | 2/2007 | |
| WO | 2009043927 | | 4/2009 | |
| WO | 2010071928 | | 7/2010 | |
| WO | 2011/144932 | | 11/2011 | |
| WO | 2012052061 | | 4/2012 | |
| WO | 2013059940 | | 5/2013 | |
| WO | 2013067230 | | 5/2013 | |
| WO | 2014/033306 | | 3/2014 | |
| WO | 2014085789 | | 6/2014 | |
| WO | 2014186620 | | 11/2014 | |
| WO | 2015024031 | | 2/2015 | |
| WO | 2015/051834 | | 4/2015 | |
| WO | 2015/072202 | | 5/2015 | |
| WO | 2015/179253 | | 11/2015 | |
| WO | 2016025583 | | 2/2016 | |
| WO | 2016074861 | | 5/2016 | |
| WO | 2016078911 | | 5/2016 | |
| WO | 2016097919 | | 6/2016 | |
| WO | 2016111880 | | 7/2016 | |
| WO | 2016146486 | | 9/2016 | |
| WO | 2016146488 | | 9/2016 | |
| WO | 2017001146 | | 1/2017 | |
| WO | 2017025486 | | 2/2017 | |
| WO | 2017027352 | | 2/2017 | |
| WO | 2017/046419 | | 3/2017 | |
| WO | 2017053966 | | 3/2017 | |
| WO | 2017053971 | | 3/2017 | |
| WO | 2017053972 | | 3/2017 | |
| WO | 2017053974 | | 3/2017 | |
| WO | 2017/096396 | | 6/2017 | |
| WO | 2017151206 | | 9/2017 | |
| WO | 2017/216118 | | 12/2017 | |
| WO | 2018000020 | | 1/2018 | |
| WO | 2018000039 | | 1/2018 | |
| WO | 2018063451 | | 4/2018 | |
| WO | 2018149875 | | 8/2018 | |

OTHER PUBLICATIONS

Marc Tonsen, Andreas Bulling et al: "InvisibleEye: Mobile Eye Tracking Using Multiple Low-Resolution Cameras and Learning-Based Gaze Estimation", Proceedings of the ACM on Interactive, Mobile, Wearable and Ubiquitous Technologies, vol. 1, No. 3, Article 106, Sep. 2017.

Mayberry, Addison, et al. "iShadow: design of a wearable, real-time mobile gaze tracker." Proceedings of the 12th annual international conference on Mobile systems, applications, and services, p. 82-94, ACM, 2014.

Mayberry PhD thesis, Leveraging Eye Structure and Motion to Build a Low-Power Wearable Gaze Tracking System, Oct. 2018.

Ishiguro, Yoshio, et al. "Aided eyes: eye activity sensing for daily life." Proceedings of the 1st Augmented Human International Conference. ACM, 2010.

Fuhl, Wolfgang, et al. "PupilNet: convolutional neural networks for robust pupil detection." arXiv preprint arXiv:1601.04902 (2016).

Baluja, Shumeet, and Dean Pomerleau. "Non-intrusive gaze tracking using artificial neural networks" Advances in Neural Information Processing Systems. 1994.

Pomplun et al. "An artificial neural network for high precision eye movement tracking", Advances in Artificial Intelligence, vol. 861 of the series Lecture Notes in Computer Science, pp. 63-69. 2005.

Zhang, Xucong, et al. "Appearance-based gaze estimation in the wild." Proceedings of the IEEE Conference on Computer Vision and Pattern Recognition. 2015.

(56) References Cited

OTHER PUBLICATIONS

Zhang, Xucong, et al. "It's written all over your face: Full-face appearance-based gaze estimation." Computer Vision and Pattern Recognition Workshops (CVPRW), 2017 IEEE Conference on. IEEE, 2017.

Feng Lu, Yusuke Sugano, Takahiro Okabe, and Yoichi Sato: "Adaptive Linear Regression for Appearance-Based Gaze Estimation", IEEE transactions on pattern analysis and machine intelligence (TPAMI) 36, 10 (2014), 2033-2046.

Cihan Topal, Serkan Gunal, Onur Koçdeviren, Atakan Doğan, and Ömer N Gerek: "A Low-Computational Approach on Gaze Estimation With Eye Touch System", IEEE transactions on Cybernetics 44, 2 (2013), 228-239.

Krafka, et al. "Eye tracking for everyone." IEEE Conference on Computer Vision and Pattern Recognition (CVPR), pp. 2176-2184, 2016.

Sugano, Bulling: "Self-calibrating head-mounted eye trackers using egocentric visual saliency." In Proc. ACM Symposium on User Interface Software and Technology (UIST 2015). 363-372.

Huang, Veeraraghavan, Sabharwal: "TabletGaze: Unconstrained appearance-based gaze estimation in mobile tablets" Jul. 16, 2016.

Hickson et al., "Eyemotion: Classifying facial expressions in VR using eye-tracking cameras", arXiv:1707.07204v2 [cs.CV] Jul. 28, 2017.

Anjith George, Aurobinda Routray: "Real-time Eye Gaze Direction Classification Using Convolutional Neural Network", IEEE InternationalConference on Signal Processing and Communication, SPCOM 2016.

Olszewski, K., Lim, J., Saito, S., Li, H.: "High-Fidelity Facial and Speech Animation for VR HMDs". ACM Trans. Graph.35, 6, Article 221 (Nov. 2016).

"Pogocam", Youtube, Jan. 6, 2017, URL: https://www.youtube.com/watc67v=pHumrhlSYx4.

Krafka, Building Real-Time Unconstrained, Eye Tracking with Deep Learning, B.S., University of Georgia, Dec. 2015. (112 pgs.).

Krafka, et al, "Eye Tracking for Everyone", University of Georgia, pp. 2176-2184, 2016. (9 pgs.).

Abstract Book—CVPR—2016 Main Conference and Workshops, 2016.

Non-Final Office Action dated Apr. 14, 2021 in U.S. Appl. No. 16/967,090.

Non-Final Office Action dated Jun. 24, 2021 in U.S. Appl. No. 16/967,363.

Notice of Allowance dated Jul. 21, 2021 in U.S. Appl. No. 16/967,090.

Non-Final Office Action dated Dec. 17, 2021 in U.S. Appl. No. 16/967,304.

Final Office Action dated Jan. 6, 2022 in U.S. Appl. No. 16/967,363.

Notice of Allowance dated Mar. 30, 2022 in U.S. Appl. No. 16/967,304.

Swirski, Dodgson: "A fully-automatic, temporal approach to single camera, glint-free 3D eye model filling", Proc. PETMEI Lund/Sweden, Aug. 13, 2013.

Safaee-Rad, R., Tchoukanov, I., Smith, K., & Benhabib, B. (1992). "Three-dimensional location estimation of circular features for machine vision", IEEE Transactions on Robotics and Automation, 8(5), 624-640.

Dierkes, Kassner, Bulling: "A novel approach to single camera, glint-free 3D eye model fitting including corneal refraction", Proc. ETRA Warsaw/Poland Jun. 2018.

Dierkes, Kassner, Bulling: "A fast approach to refraction-aware eye-model fitting and gaze prediction", Proc. ETRA Denver/USA Jun. 25-28, 2019.

Santini, Fuhl, Kasneci: "CalibMe: Fast and Unsupervised Eye Tracker Calibration for Gaze-Based Pervasive Human-Computer Interaction", Proc. CHI 2017, May 6-11, 2017.

Bace, Staal, Sörös: "Wearable Eye Tracker Calibration at Your Fingertips", Proc. ETRA 2018, Jun. 14-17, 2018, Warsaw/Poland.

\* cited by examiner

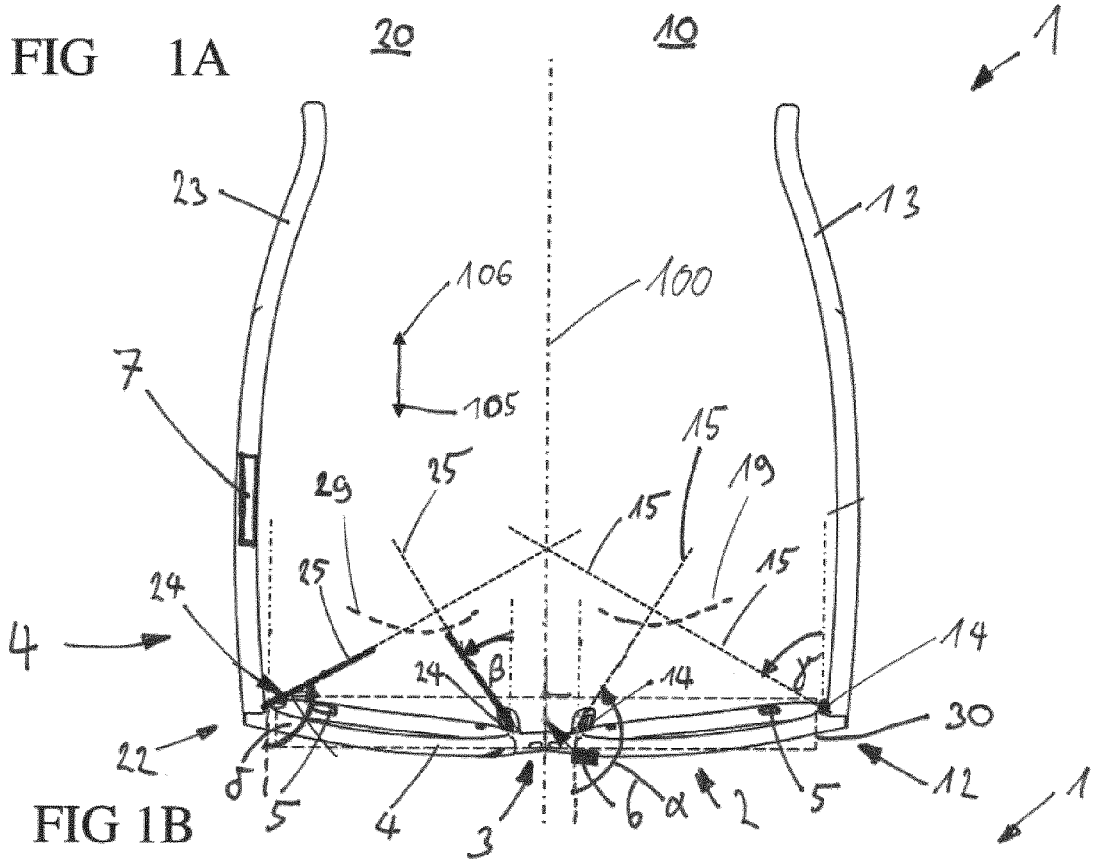
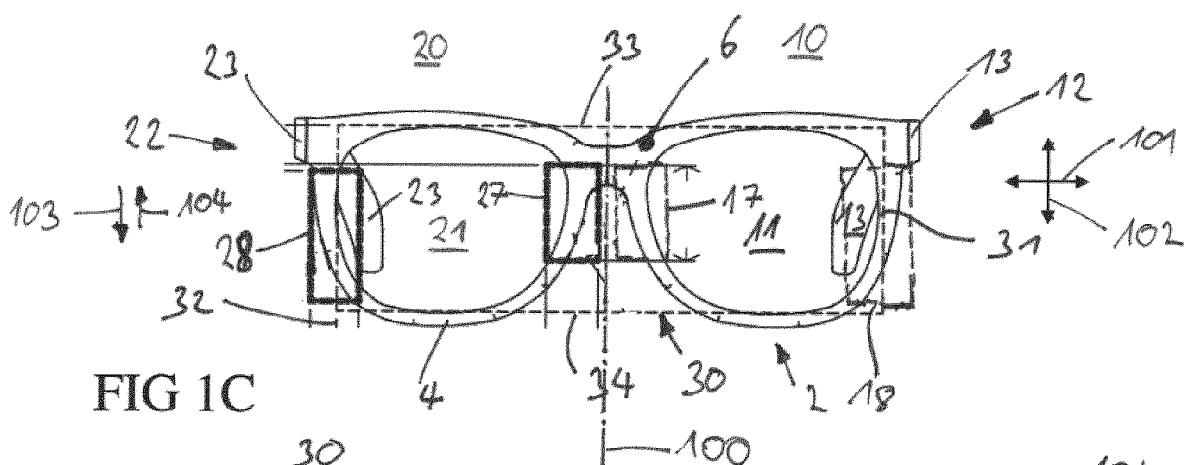
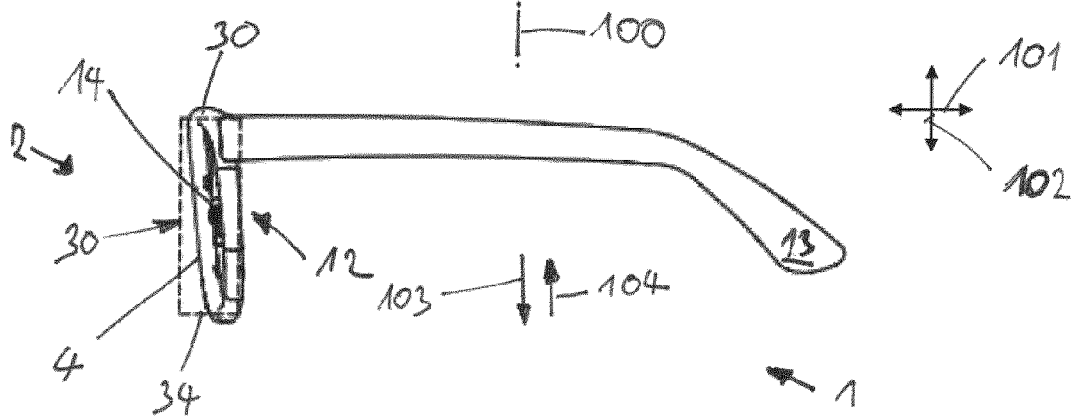

DEVICES, SYSTEMS AND METHODS FOR PREDICTING GAZE-RELATED PARAMETERS

CROSS-REFERENCE TO RELATED APPLICATIONS

This Utility Patent Application claims priority under 35 U.S.C. § 371 to International Application Serial No. PCT/EP2018/053294 filed Feb. 9, 2018, which is incorporated herein by reference in its entirety.

TECHNICAL FIELD

Embodiments of the present invention relate to a method for detecting one or more gaze-related parameters, a method for creating and updating a database for training a neural network, in particular a convolutional neural network, a method for training a neural network, a method for calibrating a head-wearable device, a related system for improving the prediction of gaze-related parameters, and a head-wearable (spectacles) device.

BACKGROUND

Current head-mounted eye trackers often rely on explicit extraction of features such as pupil center, infrared (IR) glint position, or pupil contours. Feature extraction is being performed by classic computer vision and image processing algorithms. Gaze direction is then estimated e.g. by a regression function taking the extracted features as inputs.

Feature extraction usually requires high-resolution cameras, which are rather bulky and difficult if not impossible to fully and invisibly integrate into a glasses frame. Lack of integration and occlusions of the user's field-of-view (FOV) limit the acceptability and, in turn, usability of the system and can also negatively influence users' gaze behaviour, i.e. make this behaviour unnatural. In addition, current systems require active infrared illumination of the eye to ease the task of detecting the pupil. This requires IR LEDs to be mounted close to the eye and camera, thereby adding to the chunkiness of the system. Further, the processing of high resolution images is computationally demanding. Such systems therefore require a laptop or at least a small portable computer to be worn by a user for image processing and real-time gaze estimation. Significant bandwidth for the data transfer is also required. Combined with the weight of the cameras and the remaining parts of the device (e.g. cables, camera/usb adapters, transmission/storing modules etc.), that all rest heavily on users' heads, longer recordings in everyday life are rather uncomfortable or even painful. High-resolution sensors and demanding computation, in turn, lead to high power consumption, which either sets a fixed limit to the recording duration through battery capacity, or restricts the user's ability to move around because the system requires an additional external or even wired power supply.

Even further, the camera(s) need(s) to be carefully adjusted to each individual facial geometry in order to allow e.g. for robust pupil feature detection, which requires an additional hardware-level flexibility and manual camera adjustment possibilities. For the same reason, shifts of the eye tracking headset can currently negatively impact gaze estimation accuracy or require frequent (and cumbersome) re-calibration by the user.

Also, known head mounted eye trackers suffer from the disadvantage that environmental stray light being reflected on the test user's eye may negatively influence the eye tracking functionality. In shape-based eye tracking approaches, cameras monitoring the test user's eyes may not be able to distinguish between features of the eyes explicitly used for keeping track of the eye movement and features, such as reflections, arising from environmental lighting conditions. In general, the illumination situation is not very well defined. Reliable eye tracking is often compromised by environmental conditions and undesired stray light disturbing the tracking mechanism. Thus, known head mounted eye tracker devices usually suffer from a limited accuracy and robustness.

The existing eye gaze sensing systems are also far from being widely used in consumer home applications because of two main reasons. Their cost is still high and most systems require a cumbersome and time-consuming calibration procedure. Current calibration processes may be required whenever a user's head moves beyond a threshold distance with respect to the eye tracking device from an original location at which the system was calibrated. Thus, due to the need to hold the head steady respectively to keep a rigid spatial relationship between the eye tracking device and the head or to frequently re-calibrate, current head mounted eye tracking systems using feature- and/or shape-based approaches are difficult to use in consumer settings.

Accordingly, there is a need to further improve the detection of gaze direction and other gaze-related parameters.

SUMMARY

According to an embodiment of a head-wearable spectacles device for determining one or more gaze-related parameters of a user, the head-wearable spectacles device includes a left camera for taking a left image of at least a portion of a left eye, a right camera for taking a right image of at least a portion of a right eye of the user, and a spectacles body having a middle plane and configured for being wearable on a user's head, and at least a left and a right ocular opening. Both ocular openings define a bounding cuboid having an upper surface, a lower surface, a left lateral surface, and a right lateral surface. The upper surface of the bounding cuboid is oriented perpendicular to the middle plane of the spectacles body. The cameras are arranged at the spectacles body in inner eye camera placement zones and/or in outer eye camera placement zones. The left and right inner eye camera placement zones are located in a nose bridge portion of the spectacles body and extend between 2 to 14 mm, in particular between 3 to 12 mm, in a respective direction perpendicular to the middle plane. The left outer eye camera placement zone is located in a left lateral portion of the spectacles body, and extends 6 mm, in particular 5 mm, more particular 4 mm, towards the middle plane from the left lateral surface of the bounding cuboid, and extends 7 mm, in particular 6 mm, more particular 5 mm, away from the middle plane starting from the left lateral surface. The right outer eye camera placement zone is located in a right lateral portion of the spectacles body, and extends 6 mm, in particular 5 mm, more particular 4 mm, towards the middle plane from the right lateral surface of the bounding cuboid, and extends 7 mm, in particular 6 mm, more particular 5 mm, away from the middle plane starting from the right lateral surface.

According to an embodiment of a head-wearable spectacles device for determining one or more gaze-related parameters of a user, the head-wearable spectacles device includes a spectacles body having a middle plane, a nose bridge portion, a left lateral portion, a right lateral portion, a left ocular opening and a right ocular opening. The spectacles device is configured for being wearable on a user's head. The middle plane intersects the nose bridge portion, and the respective ocular opening is located between the nose bridge portion and the respective lateral portion. The spectacles device further includes at least one of a left camera for taking a left image of at least a portion of a left eye of a user, wherein the left camera is arranged in the nose bridge portion, and wherein an optical axis of the left camera is inclined with respect to the middle plane by an angle of 150° to 142° (or −30° to −38°), in particular of 144° (or −36°), a right camera for taking a right image of at least a portion of a right eye of a user, wherein the right camera is arranged in the nose bridge portion, and wherein an optical axis of the right camera is inclined with respect to the middle plane by an angle of 30 to 38°, in particular of 36°, a left camera for taking a left image of at least a portion of a left eye of a user, wherein the left camera is arranged in the left lateral portion, and wherein an optical axis of the left camera is inclined with respect to the middle plane by an angle of 55 to 70°, in particular 62°, and/or a right camera for taking a right image of at least a portion of a right eye of a user, wherein the right camera is arranged in the right lateral portion, and wherein an optical axis of the right camera is inclined with respect to the middle plane by an angle of 125° to 110° (or −55° to −70°), in particular 118° (or −62°).

According to an embodiment of a method for creating and updating a database for training a neural network, in particular a convolutional neural network, the method includes presenting a first stimulus to a first user wearing a head-wearable device. The head-wearable device includes a first camera and a second camera. The first camera is arranged next to a left eye of the first user and the second camera is arranged next to a right eye of the first user when the first user is wearing the head-wearable device. When the first user is expected to respond to the first stimulus or expected to have responded to the first stimulus, the first camera of the head-wearable device is used to generate a first left image of at least a portion of the left eye of the first user, and a second camera of the head-wearable device is used to generate a first right image of at least a portion of the right eye of the first user. A data connection is established between the head-wearable device and the database. A first dataset including the first left image, the first right image and a first representation of a gaze-related parameter is generated. The first representation is correlated with the first stimulus. The first dataset is added to the database.

According to an embodiment of a method for training a neural network, in particular a convolutional neural network, the method includes providing a database comprising a plurality of datasets, the datasets comprising a respective left image, a respective right image and a respective corresponding representation of a gaze-related parameter, in particular a respective corresponding value of the gaze-related parameter. A neural network having a given architecture is provided. Parameters of the neural network are determined using the respective left images and the respective right images of a sub-set or of all datasets as input and the respective corresponding representations of the gaze-related parameter of the sub-set or of all datasets as desired output of the neural network.

According to an embodiment of a method for calibrating a head-wearable device, the method includes presenting a stimulus to a user wearing the head-wearable device. The stimulus is correlated with a desired value of a gaze-related parameter. The head-wearable device includes a first camera and a second camera. The first camera is arranged next to a left eye of the user and the second camera is arranged next to a right eye of the user when the user is wearing the head-wearable device. The first camera is used to generate a left image of at least a portion of the left eye of the user and the second camera is used to generate a right image of at least a portion of the right eye of the user wearing the head-wearable device and being expected to respond to the stimulus or expected to have responded to the stimulus. A trained neural network, in particular a trained convolutional neural network, is used to determine a predicted value of the gaze-related parameter using the right image and the left image as an input for the trained neural network. The desired value of the gaze-related parameter and the predicted value of the gaze-related parameter are used to determine a correction function for the user. Optionally, the correction function for the user is stored.

According to an embodiment of a system for improving the prediction of gaze-related parameters, the system includes at least one head-mountable device, a processing unit, and a computing system connectable with the processing unit and configured to host a first database and to train the neural network, in particular a convolutional neural network, using the first database. The at least one head-mountable device includes a first camera for generating a left image of at least portion of a left eye of a user and a second camera to generate a right image of at least portion of a right eye of the user when the user is wearing the head-mountable device. The processing unit is connectable with the first camera and the second camera, and configured to determine a predicted value of a gaze-related parameter of the user using the left image and the right image as input of the neural network. The system is configured to add datasets to the first database and to transfer parameters of the neural network from the computing system to the processing unit. The datasets includes a respective left image, a respective right image and a respective representation of the gaze-related parameter of the user.

According to an embodiment of a method for detecting one or more gaze-related parameters of a user, the method includes creating a left image of at least a portion of a left eye of the user using a first camera of a head-wearable device worn by the user, creating a right image of at least a portion of a right eye of the user using a second camera of the head-wearable device, feeding the left and right images together as an input into a convolutional neural network, and obtaining the one or more gaze-related parameters from the convolutional neural network as a result of the left and right images input.

Other embodiments include corresponding computer systems, computer-readable storage media or devices, and computer programs recorded on one or more computer-readable storage media or computer storage devices, each configured to perform the processes of the methods described herein.

A system of and/or including one or more computers can be configured to perform particular operations or processes by virtue of software, firmware, hardware, or any combination thereof installed on the one or more computers that in operation may cause the system to perform the processes. One or more computer programs can be configured to perform particular operations or processes by virtue of including instructions that, when executed by a one or more processors of the system, cause the system to perform the processes.

Those skilled in the art will recognize additional features and advantages upon reading the following detailed description, and upon viewing the accompanying drawings.

BRIEF DESCRIPTION OF THE DRAWINGS

The components in the figures are not necessarily to scale, instead emphasis being placed upon illustrating the principles of the invention. Moreover, in the figures, like reference numerals designate corresponding parts. In the drawings:

FIG. 1A illustrates a top view of a generalised embodiment of a head-wearable spectacles device for determining one or more gaze-related parameters according to at least one embodiment;

FIG. 1B shows the front view on the spectacles device according to FIG. 1A;

FIG. 1C is a lateral view on the spectacles device according to FIG. 1A

DETAILED DESCRIPTION

Figure 2A:
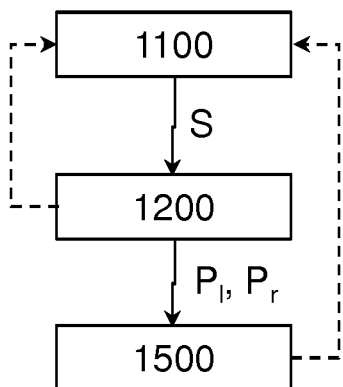
FIG. 2A illustrates a flow chart of a method for creating and updating a database for training a neural network according to embodiments.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is a task of the invention to provide methods, systems and devices allowing for determining of one or more gaze-related parameters of a user with improved performance and/or improved functional and/or ergonomic characteristics.

Said tasks are solved by the subject matter of the intendent claims.

In particular, a spectacles device comprises a spectacles body, which is configured such that it can be worn on a head of a user, for example in a way usual glasses are worn. Hence, the spectacles device when worn by a user may in particular be supported at least partially by a nose area of the user's face.

This state of usage of the spectacles device being arranged at the user's face will be further defined as the "intended use" of the spectacles device, wherein direction and position references, for example horizontal and vertical, parallel and perpendicular, left and right, front and back, up and down, etc., refer to this intended use. As a consequence, lateral positions as left and right, an upper and lower position, and a front/forward and back/backward are to be understood from user's usual view. Equally, this applies to a horizontal and vertical orientation, wherein the user's head during the intended use is in a normal, hence upright, non-tilted, non-declined and non-nodded position.

According to an embodiment, the spectacles body comprises a left ocular opening and a right ocular opening, which mainly come with the functionality of allowing the user to look through these ocular openings. Said ocular openings can be embodied, but not limited to, as sunscreens, optical lenses or non-optical, transparent glasses or as a non-material, optical pathway allowing rays of light passing through.

According to a further aspect of the invention, the spectacles body forms, at least partially or completely, the ocular openings by delimiting these from the surrounding. In this case, the spectacles body functions as a frame for the optical openings. Said frame is not necessarily required to form a complete and closed surrounding of the ocular openings. Furthermore, it is possible that the optical openings themselves have a frame like configuration, for example by providing a supporting structure with the help of transparent glass. In the latter case, the spectacles device has the form similar to frameless glasses, wherein only a nose support/bridge portion and ear-holders are attached to the glass screens, which therefore serve simultaneously as an integrated frame and as optical openings.

In addition, a middle plane of the spectacles body can be identified. In particular, said middle plane describes a structural centre plane of the spectacles body, wherein respective structural components or portions, which are comparable or similar to each other, are placed on each side of the middle plane in a similar manner. When the spectacles device is in intended use and worn correctly, the middle plane coincides with a median plane of the user.

According to a particular embodiment of the invention, the spectacles body comprises a nose bridge portion, a left lateral portion and a right lateral portion, wherein the middle plane intersects the nose bridge portion, and the respective ocular opening is located between the nose bridge portion and the respective lateral portion.

For orientation purposes, a plane being perpendicular to the middle plane shall be defined, which in particular is oriented vertically, wherein said perpendicular plane is not necessarily firmly located in a defined forward or backward position of the spectacles device.

With the help of both ocular openings a bounding cuboid is defined, which in the following shall serve as an artificial reference system for geometrical design data; thus, said bounding cuboid is a virtual, non-embodied structure having by definition an upper surface, a lower surface, a left lateral surface, and a right lateral surface; hence, one cannot identify the cuboid at the spectacles device in form of a real, cuboid body. The bounding cuboid is oriented with respect to the middle plane of the spectacles body such, that at least the upper surface is perpendicular to the middle plane.

According to an embodiment, the bounding cuboid is a rectangular cuboid; hence, the upper and the lower surface are both perpendicular to the middle plane, and the left and right lateral surface are both oriented parallel with regard to the middle plane.

In the following supporting clarifications and explanations about the artificial reference system "bounding cuboid" is provided to the skilled user, in particular in a non-limiting manner: The definition of the bounding cuboid by the ocular openings is performed by virtually covering the volume of both ocular openings with a cuboid, in particular wherein the left lateral surface of the bounding cuboid touches the left ocular opening from the left side, the right lateral surface of the cuboid touches the right ocular opening from the right side, the upper surface of the cuboid touches at least one of the ocular openings from above, and wherein the lower surface of the cuboid touches at least one of the ocular openings from below. As a consequence, the ocular openings do not protrude from the boundary surfaces of the bounding cuboid, and the size of the bounding cuboid does not exceed beyond the maximum extension of the ocular openings.

According to the invention, the spectacles device comprises a left and a right camera, wherein the left camera serves for taking a left image or a stream of images of at least a portion of the left eye the user, and wherein the right camera takes an image or a stream of images of at least a portion of a right eye of the user. The recorded images do not necessarily need to be a picture as visible by the human eye, but can also be an appropriate representation of the filmed eye in a range of light non-visible for humans.

The cameras can be arranged at the spectacles body in inner eye camera placement zones and/or in outer eye camera placement zones, in particular wherein said zones are determined such, that an appropriate picture of at least a portion of the respective eye can be taken for the purpose of determining one or more a gaze-related parameter; in particular, the cameras are arranged in a nose bridge portion and/or in a lateral edge portion of the spectacles frame such, that an optical field of a respective eye is not obstructed by the respective camera. The optical field is defined as being obstructed, if the camera forms an explicitly visible area/portion within the optical field, for example if the camera points out from the boundaries of the visible field into said field, or by protruding from the boundaries into the field. For example, the cameras can be integrated into a frame of the spectacles body and thereby being non-obstructive. In the context of the present invention, a limitation of the visible field caused by the spectacles device itself, in particular by the spectacles body or frame is not considered as an obstruction of the optical field.

According to an embodiment of the spectacles device, the cameras are arranged in the inner eye camera placement zones only, in particular wherein not more than one single camera is provided in each inner eye camera placement zone; hence, there is only one left camera firmly associated to the left ocular opening, and only one right camera firmly associated to the right ocular opening.

The inner eye camera placement zones may be allocated in a nose bridge portion of the spectacles body. In detail, it has been found out by extensive experiments and user tests that the respective inner eye camera placement zone shall extend between 2 mm to 14 mm, in particular between 3 mm to 12 mm, in a horizontal direction perpendicular to the middle plane in order to obtain optimal images for determining the one or more gaze-related parameter. In particular, the inner eye camera placement zones can be located and do extend in the perpendicular plane, wherein—starting from the middle plane in the left and right horizontal direction—the respective inner eye camera placement zone begins in a horizontal direction at a distance of 2 mm, in particular 3 mm, from the middle plane, and reaches in horizontal direction towards a distance of 14 mm, in particular 12 mm, from the middle plane.

According to an alternative or to an addition, at least one camera or both cameras can be arranged in (an) outer eye camera placement zone(s). In particular, the spectacles device comprises not more than two cameras, wherein the right camera is arranged in the right outer eye camera placement zone, and wherein the left camera is arranged in the left outer eye camera placement zone.

According to an embodiment, the left camera is placed in the left outer eye camera placement zone, and the right camera is placed in the right outer eye camera placement zone, or the left camera is placed in the left inner eye camera placement zone, and the right camera is placed in the right inner eye camera placement zone. This symmetric camera placement strategy results in an improved capability of determining a gaze-related parameter of the user, in particular if the light conditions of an environment of the spectacles device are not optimal. Furthermore, the symmetric application of cameras may also come with benefits with respect to the application of neuronal networks, in particular convolutional neuronal networks, for determining a gaze-related parameter. According to another embodiment, more than one left and/or more than one right camera may be used.

The left outer eye camera placement zone—when projected in the perpendicular plane—is located in a left lateral portion of the spectacles body, and extends 6 mm, in particular 5 mm, more particular 4 mm, towards the middle plane from the left lateral surface of the bounding cuboid, and extends 7 mm, in particular 6 mm, more particular 5 mm, away from the middle plane measured from the left lateral surface in a direction away from the middle plane.

Also, the right outer eye camera placement zone—when projected in the perpendicular plane—is located in a right lateral portion of the spectacles body, and extends 6 mm, in particular 5 mm, more particular 4 mm, towards the middle plane from the right lateral surface of the bounding cuboid, and extends 7 mm, in particular 6 mm, more particular 5 mm, away from the middle plane measured from the right lateral surface in a direction away from the middle plane.

According to a further embodiment, the inner eye camera placement zone extends, when projected in the perpendicular plane, in vertical direction between 9 to 31 mm, in particular 12 to 28 mm, from the upper surface towards the lower surface of the bounding cuboid.

Additionally or alternatively, the outer eye camera placement zone—projected in the perpendicular plane—has a size of 25 to 33 mm, particular of 28 to 30 mm, in a perpendicular direction with respect to the upper surface, and, when the spectacles device is in intended use, in vertical direction.

It has been found out that the upper task is independently solved in an alternative or additional way by a spectacles device according to claim 6.

Definitions, directions and basic information of the spectacles device as described above shall apply also in the following. In particular, such spectacles device according to claim 6 comprises a spectacles body, which is configured such, that it can be worn on a head of a user, for example in a way usual glasses are worn.

According to an embodiment of the spectacles device, it comprises a spectacles body having a middle plane (see above), a nose bridge portion, a left lateral portion, a right lateral portion, a left ocular opening and a right ocular opening.

As discussed above, the nose bridge portion is an area of the spectacles device, which serves as the support for the device on the nose region of the user, and meanwhile being arranged in between the left and the right ocular opening. The left/right lateral portion represents a structural area of the device, which is located left/right of the left/right ocular opening. Thus, the respective left/right ocular opening lies in between the nose bridge portion and the respective left/right lateral portion.

Furthermore, the spectacles device has at least a left camera for taking a left image of at least a portion of a left eye of the user, and at least a right camera for taking a right image of at least a portion of a right eye of the user.

According to a first design, the left camera is arranged in the nose bridge portion, wherein an optical axis of the left camera is inclined with respect to the middle plane by an angle of 150° to 142° (or −30° to −38°), in particular of 144° (or −36°). Generally, angles of the inclination are provided and shall be measured positive in counter-clockwise direction.

According to a second design, the right camera is arranged in the nose bridge portion, wherein an optical axis of the right camera is inclined with respect to the middle plane by an angle of 30° to 38°, in particular of 36°.

Both designs come with the benefit, that an optimal view of the cameras onto an eyeball of the user is enabled, wherein an obstruction of the visible field of the user is essentially not noticeable by the user and therefore is not present; firstly, the human mind mostly ignores any obstruction in the nose area of the face, because the nose itself forms a permanent obstruction of the optical field; secondly, the nose bridge portion usually serves as a support for the spectacles device on the nose of a user, wherein a microcamera can be integrated in support elements of the nose portion.

According to a third design, the left camera is arranged in the left lateral portion, wherein an optical axis of the left camera is inclined with respect to the middle plane by an angle of 55° to 70°, in particular 62°.

According to a fourth design, the right camera is arranged in the right lateral portion, wherein an optical axis of the right camera is inclined with respect to the middle plane by an angle of 125° to 110° (or −55° to −70°), in particular 118° (or −62°).

According to a first preferred embodiment, the spectacles device comprises not more than two cameras, wherein one camera—the left camera—is arranged according to the first design, and wherein the other camera—the right camera—is arranged according to the second design.

In the context of a second preferred embodiment, the spectacles device comprises not more than two cameras, wherein one camera—the left camera—is arranged according to the third design, and wherein the other camera—the right camera—is arranged according to the fourth design.

However, the combination of the first and the third design or of the second and the fourth design is also possible.

Furthermore, but not limited to it, a combination of at least three of the designs, or even of all designs shall be disclosed in the context of the invention, wherein the limitation on not more than two cameras is therefore omitted in this very case.

All mentioned designs, in particular combinations thereof, provide a spectacles device for obtaining suitable image data for determining one or more gaze-related parameters of the user, in particular when applying a convolutional neuronal network for this determination.

In the following, preferred embodiments of the invention are described, wherein said embodiments refer to all previously discussed embodiments of the spectacles device, in particular to the spectacles device according to claim 1 and/or according to claim 6.

Furthermore, it is explicitly included, that a spectacles device according to claim 6 may also include one or a plurality of features of a spectacles device according to claim 1 to 5. For example, the spectacles device according to claim 6—incorporating angles of the optical axis of the cameras—includes fully or partially a specification of the left/right, outer/inner camera placement zone and related distances. Vice versa, the spectacles device according to claim 1—mainly defined by the camera position in camera placement zones—may include one or more specific features of the inclination of the optical axis of one or more cameras.

According to a non-limiting embodiment, the spectacles body of the spectacles device according to one or more embodiments as described above has at least partially a symmetrical structure with respect to the middle plane. In particular, at least a functional-structural area of a nose portion and/or of a left and right lateral portion of the spectacles body is/are symmetrical; as an example, said functional-structural area may be a support element of the nose portion or a plurality thereof, which support the spectacles device on a nose region of the user, a respective inner, lateral, upper and/or lower part of the spectacles body, or can be a holder or hinge element in the left and right lateral portion for supporting the spectacles body on user's ear.

Furthermore, according to a particular embodiment, a frame of the spectacles body is essentially symmetrical to the middle plane, wherein only minor areas, portions or elements of the frame are non-symmetrical.

According to specific embodiment, the cameras are arranged within the lower 75%, in particular within the lower 50%, preferred within the lower 25%, of the volume of the bounding cuboid.

Furthermore, according to an embodiment having at least one camera placed in a lateral portion of the body and/or in one of the outer eye camera placement zones, said camera is arranged in a frame of the spectacles body, in a respective left or right holder, which serves as a support for the spectacles device on an ear of the user, or in/at a hinge element, which connects the holder to the frame of the spectacles body. By applying this teaching, the camera(s) can be arranged very discreetly and non-obtrusively in the spectacles body, while a beneficial view on to the eyeball of the user is obtained.

According to embodiments, the spectacles device may have illumination means for illuminating the left and/or right eye of the user, in particular if the light conditions within an environment of the spectacles device are not optimal.

According to an embodiment, the spectacles device comprises a scene camera for taking images of a field of view of the user wearing the spectacles device. The scene camera hence must not be understood as a camera for taking a picture of an eye of the user. By this a beneficial calibration process of the determination of the gaze-related parameter can be made possible. The calibration process is described below with regard to FIG. 3C.

For reliably and efficiently analyzing the images of the left and right cameras with respect to gaze-related parameters, training the used neuronal network architecture with a large number of teaching examples is desirable. For this purpose, a respective database for storing the teaching examples obtained with the help of the spectacles device and/or other head-wearable device as described herein has been found to be advantageous.

According to an embodiment, a method for creating and updating a database for training a neural network, in particular a convolutional neural network, is provided. The method includes presenting a first stimulus to a first user wearing a head-wearable device. The head-wearable device includes a first camera and a second camera. The first camera is arranged next to a left eye of the first user and the second camera is arranged next to a right eye of the first user when the first user is wearing the head-wearable device. When the first user is expected to respond to the first stimulus or expected to have responded to the first stimulus, the first camera of the head-wearable device is used to generate a first left image of at least a portion of the left eye of the first user, and a second camera of the head-wearable device is used to generate a first right image of at least a portion of the right eye of the first user. A data connection is established between the head-wearable device and the database. A first dataset including the first left image, the first right image and a first representation of a gaze-related parameter is generated. The first representation is correlated with the first stimulus. The first dataset is added to the database.

The method allows maintaining and improving the database with the help of the users. As the database can be used for improving the performance of an instance of the neural network used at the user site (e.g. running on the head-wearable device), the users are interested in allowing data exchange between the typically user owned head-wearable device and a computing system for hosting the database and training or retraining the neural network using the database.

In the following the database is also referred to as first database and image database.

Within this specification the terms "first camera" and "left camera" are used synonymously. Likewise, the terms "second camera" and "right camera" are used synonymously herein.

The term "neural network" (NN) as used in this specification intends to describe an artificial neural network (ANN) or connectionist system including a plurality of connected units or nodes called artificial neurons. The output signal of an artificial neuron is calculated by a (non-linear) activation function of the sum of its inputs signal(s). The connections between the artificial neurons typically have respective weights (gain factors for the transferred output signal(s)) that are adjusted during one or more learning phases. Other parameters of the NN that may or may not be modified during learning may include parameters of the activation function of the artificial neurons such as a threshold. Often, the artificial neurons are organized in layers which are also called modules. The most basic NN architecture, which is known as a "Multi-Layer Perceptron", is a sequence of so called fully connected layers. A layer consists of multiple distinct units (neurons) each computing a linear combination of the input followed by a nonlinear activation function. Different layers (of neurons) may perform different kinds of transformations on their respective inputs. Neural networks may be implemented in software, firmware, hardware, or any combination thereof. In the learning phase(s), a machine learning method, in particular a supervised, unsupervised or semi-supervised (deep) learning method may be used. For example, a deep learning technique, in particular a gradient descent technique such as backpropagation may be used for training of (feedforward) NNs having a layered architecture. Modern computer hardware, e.g. GPUs makes backpropagation efficient for many-layered neural networks. A convolutional neural network (CNN) is a feed-forward artificial neural network that includes an input (neural network) layer, an output (neural network) layer, and one or more hidden (neural network) layers arranged between the input layer and the output layer. The speciality of CNNs is the usage of convolutional layers performing the mathematical operation of a convolution of the input with a kernel. The hidden layers of a CNN may include convolutional layers as well as optional pooling layers (for downsampling the output of a previous layer before inputting it to the next layer), fully connected layers and normalization layers. At least one of the hidden layers of a CNN is a convolutional neural network layer, in the following also referred to as convolutional layer. Typical convolution kernel sizes are for example 3×3, 5×5 or 7×7. The usage of convolutional layer(s) can help to compute recurring features in the input more efficiently than fully connected layers. Accordingly, memory footprint may be reduced and performance improved. Due to the shared-weights architecture and translation invariance characteristics, CNNs are also known as shift invariant or space invariant artificial neural networks (SIANNs). In the following, the term "model of a neural network" intends to describe a set of data required to define a neural network operable in software and/or hardware. The model typically includes data referring to the architecture of the NN, in particular the network structure including the arrangement of neural network layers, the sequence of information processing in the NN, as well as data representing or consisting of parameters of the NN, in particular the connection weights within fully connected layers and kernel weights within convolutional layers.

Traditional eye tracking algorithms extract hand crafted features from the eye images, like for example the pupil contour. The observed features are then used to either fit an eye model to the observations, or to directly regress the output.

In contrast, the systems described herein perform end-to-end learning-based gaze estimation, where the input image is directly given to a learning algorithm without prior extraction of handcrafted features.

In a training phase, the network learns to interpret the input image(s) automatically in order to output the correct result. Supervised learning algorithms, such as those employing neural networks (NN) rely on the existence of so-called labeled data, i.e. some kind of input data in combination with ground truth connected to that input data. For example, an image recorded by a camera can represent the input data. The ground truth value or values can be any low or high level piece of information which is encoded in any form in the input data and which is known at the time the input data has been generated.

For example, a user wearing a head-wearable device as shown in FIG. 1A to FIG. 1C can be asked to look at a particular marker point or object in space, the coordinates of which within the video images recorded by a scene camera connected to the device can be precisely determined. The image or images recorded by one or more optical sensors (cameras) facing the eye(s) of the person then represent the input data which encodes the information about the person's gaze direction, while said coordinates represent the ground truth. Having the person look at markers in many different directions and distances thus produces ground truth for all possible gaze directions. Collecting large amounts of labelled data, also called training data, thus forms the basis for training a learning algorithm.

A NN typically implements a mathematical model with a large number of parameters, which is set up to receive an entity of input data (for example the pixel values of an image stretched into a 1-dimensional vector) and calculates a prediction output in a format corresponding to the ground truth (for example a pair of (x/y) coordinates). The parameters (weights) of the network are usually randomly initialized. The goal of the training procedure is then to optimize the parameters such that when a training example is input, its ground truth value is correctly output. Furthermore, when training is finished, a new entity of labeled input data, also called test data, which has not been used for training, is supposed to produce a correct prediction when fed into the network. The training procedure is done by feeding training examples into the network and for example summing the absolute deviations of the output predictions from the ground truths, which yields a cost value or function. Numerical methods are used to minimize this cost in an iterative fashion which updates the parameters of the network model (backpropagation, gradient descent). A learning rate parameter is part of such methods in order to update the parameters. During the neural network training one typically incrementally decreases the learning rate (learning rate decay), i.e. the step size of the gradient descent algorithm. Decreasing the learning rate following a cosine curve has turned out to be beneficial in significantly reducing training time without impacting accuracy negatively.

The training process can for example be stopped once a desired prediction accuracy based on a set of test data examples is achieved or once the cost does not substantially decrease further. The final values of the parameters can then be digitally stored as a "model" and applied to a new input data example to generate a prediction. Depending on the amount of training data and the complexity of the model, training can be a process requiring several hours or days of calculation time, even when parallelized on many GPUs, while applying the model in a forward pass on a single item of input data is supposed to be quasi instantaneous.

For a regression problem, i.e. a problem with continuous output space like for example predicting a pair of (x/y) coordinates, one typically designs neural networks as follows:

Input→some neural network layers→Intermediate Feature Representation→Linear Combination→Output in $\mathbb{R}^2$ (respectively some small subset of $\mathbb{R}^2$).

A different approach that has shown to increase accuracy works as follows: discretize the output space, i.e. a small subset of $\mathbb{R}^2$, to k different values. Instead of directly regressing the output (for example predicting a pair of (x/y) coordinates), one computes a probability distribution over the possible output values k. As a final output one computes the weighted mean of all values, weighted by their respective probability. The information flow thus becomes:

Input→some neural network layers→Intermediate Feature Representation→Linear Combination→Output in $\{1, \ldots, k\}$→Softmax→Probability distribution P over $\{1, \ldots, k\}$→weighted mean of $\{1, \ldots, k\}$ with P→Output within the small subset of $\mathbb{R}^2$.

Enforcing the representation as a probability distribution as an intermediate result seems to have a regularizing effect and as such reduces the prediction error of the network.

Establishing the data connection typically includes connecting the head-wearable device with a computing system operating as a server hosting the database. The head-wearable device may be directly connected with the computing system (server), for example via WLAN and/or an internet connection, or indirectly, for example via a desktop computer, a tablet, a laptop, or a smartphone (mobile phone) connectable with the head-wearable device and the computing system.

Typically, a plurality of datasets referring to the first user and including a respective left image, a respective right image and a respective representation of the gaze-related parameter is generated and added to (stored in) the database.

Accordingly, the database includes datasets of the user allowing a sufficiently good feature generalisation of the neural network during one or more training phases as well as a high accuracy of predicting gaze-related parameters using the trained neural network.

For example, at least 10 datasets, more typically at least 50 datasets and even more typically at least hundred datasets of the first user may be stored in the database.

For this purpose, a second stimulus may be presented to the first user wearing the head-wearable device and the first camera of the head-wearable device may be used to generate, when the first user is expected to respond to the second stimulus or expected to have responded to the second stimulus, a second left image of at least a portion of the left eye of the first user, and using, when the first user is expected to respond to the second stimulus or expected to have responded to the second stimulus, the second camera of the head-wearable device to generate a second right image of at least a portion of the right eye of the first user. A second dataset including the second left image, the second right image and a second representation of the gaze-related parameter, the second representation being correlated with the second stimulus may be generated and added to the database.

Furthermore, the images of the datasets of the first user may be generated under different conditions, for example for a fresh and a tired user or at different times and/or for different lighting conditions. Even further, the images of the datasets of the first user may be generated for different distances between a presented stimulus and the user (resulting in different levels of vergence of the eyes).

Therefore, one or more sequences of stimuli may be presented to the first user and respective datasets may be generated and added to the database.

For statistical reasons some of the stimuli may be equal.

For example, the first and/or the second stimulus may be presented twice or more often to the first user.

Depending on the stimulus, a certain time delay may occur between the stimulus and the desired response of the user. The time delay may be in a range from 100 ms or 200 ms to about half a second or even a second.

For example, when a user is requested to look at a non-moving object or marker in his FOV, the user may be expected to have responded after the time delay and gaze thereafter at the object or marker for a time period of about half a second.

When a user is, in response to a respective stimulus, gazing at one of his moving fingertips, the time delay may even be insignificant during the movement. Accordingly, the user may be expected to respond to the stimulus during the movement of the fingertip.

Furthermore, generating the respective dataset typically includes selecting a pair of left and right images from respective video streams or image sequences obtained using the respective first and second cameras.

For example, when a user is requested to look at a non-moving object or marker in his FOV, selecting the image pair respectively ensuring its validity may include determining automatically that the gaze of the user has become stable or analysing the trajectory of the predicted gaze or utilising a separate mechanism, such as for example a separately trained neural network, for saccade or fixation detection.

Furthermore, a video stream or image sequence may be used to generate a plurality of datasets. For example, datasets referring to different gaze points/gaze directions may be generated using a video stream or image sequence obtained with (e.g. recorded with) the first camera, using a video stream or image sequence obtained with the second camera, and a video stream or image sequence obtained with a scene camera of a respective head-wearable device.

Typically, respective datasets referring to several users are generated and added to (stored in) the database.

Accordingly, the feature generalisation of the neural network in the training phase as well as the accuracy of predicting gaze-related parameters using the trained neural network may be further improved as more and more datasets from an increasing number of users and recorded under varying conditions are added.

Typically, datasets referring to at least 10 users, more typically to at least 100 users and even more typically to at least several hundred, several thousand or even several 10,000 users or more may be stored in the database.

For example, a third stimulus may be presented to a second user wearing the head-wearable device. The first camera of the head-wearable device may be used to generate, when the second user is expected to respond to the third stimulus or expected to have responded to the third stimulus, a third left image of at least a portion of a left eye of the second user, and the second camera of the head-wearable device may be used, when the second user is expected to respond to the third stimulus or expected to have responded to the third stimulus, to generate a third right image of at least a portion of a right eye of the second user. Thereafter, a third dataset including the third left image, the third right image and a third representation of the gaze-related parameter, the third representation being correlated with the third stimulus, may be generated and added to the database.

Likewise, a fourth stimulus may be presented to the first user, the second user or a third user wearing a further head-wearable device. The further head-wearable device includes a first camera arranged next to the left eye of the respective user and a second camera arranged next to the right eye of the respective user when the respective user is wearing the further head-wearable device. The first camera of the further head-wearable device may be used to generate, when the respective user is expected to respond to the fourth stimulus or expected to have responded to the fourth stimulus, a fourth left image of at least a portion of the left eye of the respective user, and the second camera of the further head-wearable device may be used to generate a fourth right image of at least a portion of the right eye of the respective user. A data connection between the further head-wearable device and the database may be established. A fourth dataset including the fourth left image, the fourth right image and a fourth representation of the gaze-related parameter, the fourth representation being correlated with the fourth stimulus; may be generated and added to the database.

The dataset(s) may be generated at the user side, for example using a processing unit of the respective head-wearable device and/or of a connected desktop computer, tablet, laptop, or smartphone.

Further, the dataset(s) may be locally stored until a connection with the computing system (server) is available.

Furthermore, the first camera of the head-wearable device or the further head-wearable device may be used to generate a further left image of at least a portion of the left eye of the first or the second user and the second camera of the respective head-wearable device may be used to generate a further right image of at least a portion of the right eye of the respective user, when the respective user is expected to respond to the further stimulus or expected to have responded to the further stimulus. A further dataset including the further left image and the further right image may be generated and added to the database.

The authors have found out, that a certain fraction of weakly labelled datasets, i.e. datasets with less accurate known gaze-related parameters, or even non-labelled datasets, i.e. datasets for which no valid representations, e.g. values of the gaze-related parameter(s) are known, can still improve the performance of the NN trained using the database. This is because even unlabeled datasets include information about the contained image diversity.

For example, the database may include up to 70%, more typically up to 80%, and even more typically up to 90% or more of weakly and/or non-labelled datasets.

In one embodiment, more than one gaze-related parameter, for example two or three gaze-related parameters are added with at least one of the datasets to the database.

The term "gaze-related parameter" as used within this specification intends to describe a gaze direction, a cyclopean gaze direction, a 3D gaze point, a 2D gaze point, eye pose as 3D position and orientation, a pair of 3D gaze directions (left and right eye), a visual axis orientation, an optical axis orientation, a pupil axis orientation, a line of sight orientation, an orientation and/or a position and/or an eyelid closure, a pupil area, a pupil size, a pupil diameter, a sclera characteristic, an iris diameter, a characteristic of a blood vessel, a cornea characteristic of at least one eye, a cornea radius, an eyeball radius, a distance pupil-center to cornea-center, a distance cornea-center to eyeball-center, a distance pupil-center to limbus center, a cornea keratometric index of refraction, a cornea index of refraction, a vitreous humor index of refraction, a distance crystalline lens to eyeball-center, to cornea center and/or to corneal apex, a crystalline lens index of refraction, a degree of astigmatism, an orientation angle of a flat and/or a steep axis, a limbus major and/or minor axes orientation, an eye cyclo-torsion, an eye intra-ocular distance, an eye vergence, statistics over eye adduction and/or eye abduction, statistics over eye elevation and/or eye depression, data about cognitive load, blink events, drowsiness and/or awareness of the user, and, a parameter for the user iris verification and/or identification. Points and directions can be specified for example within a scene camera image, an eye camera coordinate system, scene camera coordinate system, device coordinate system, head coordinate system, world coordinate system or any other suitable coordinate system.

According to an embodiment, a respective given or resulting value of the gaze-related parameter(s) is determined for the respective user expected to respond or have responded to the respective stimulus.

The determined given or resulting value of the gaze-related parameter(s) may be used as respective representation of the gaze-related parameter(s) of the dataset(s).

The determined given or resulting value may be considered as the actual or ground truth value of the gaze-related parameter.

In the following, a dataset which includes a left image of at least a portion of the left eye, a right image of at least a portion of the right eye and a corresponding actual or ground truth value of one or more a gaze-related parameters such as the gaze point or gaze direction is also referred to as labelled dataset. Typically, the two images of a dataset are taken at substantially the same time, i.e. within a time period of at most 50 ms or even at most 10 ms.

Labelled datasets are particularly valuable for training NNs.

According to embodiments, a gaze-related parameter determination unit, in particular a respective unit of the respective head-wearable device is used to determine the respective given or resulting value of the gaze-related parameter, in particular the respective given or resulting gaze direction and/or the respective given or resulting gaze point for the respective user.

In one embodiment, a scene camera arranged to capture a given object in the field of view of the respective user wearing the respective head-wearable device is used for capturing images which can be used as a basis for determining a respective resulting value of the gaze-related parameter.

For example, in response to a respective stimulus, e.g. a visual stimulus and/or an acoustical stimulus, the respective user is caused to gaze/gazes at a given respective object defining a respective given gaze direction relative to a co-ordinate system fixed with the respective head-wearable device and/or a respective given gaze point in the co-ordinate system.

According to an exemplary embodiment, the respective user is requested by a visual stimulus or an acoustical stimulus to look at a marker or object, for example a tip of one of his fingers.

As already explained above, the respective user may be requested to look at his fingertip held in different positions, or to follow his fingertip with the eyes while moving. Therefore, even a single stimulus may be used to generate a sequence of datasets each including a respective left image, a respective right image and a different resulting value of the respective gaze-related parameter(s) as representation of the gaze-related parameter(s).

A respective left image and a respective right image may be generated, when the respective user is expected to gaze at the respective given object, into the respective given direction and/or at the respective given gaze point.

Thereafter, the resulting value(s) of the given gaze direction and/or the given gaze point in the co-ordinate system fixed with the respective head-wearable device may be determined using a scene image of the user's field of view (FOV) when the respective user is expected to gaze at the respective given object, into the respective given direction and/or at the respective given gaze point. The scene image may be obtained using the scene camera.

Furthermore, determining and storing the resulting value(s) in the co-ordinate system fixed with the respective head-wearable device facilitate their later use.

Determining the resulting value(s) may be achieved using state-of-the-art machine learning, computer vision or image recognition techniques.

Of course, it is assumed that the user(s) operates in a cooperative manner. Such behaviour can be assumed, as each user has an interest in improving the accuracy and robustness of the predictions of the NN which is trained/retrained using the database, and thus depend on the quality of the datasets provided by the user(s).

This applies also to a further embodiment in which a desired value of the gaze-related parameter is used to determine the position and/or appearance of an object to be displayed in the user's FOV. In the following, the desired value of the gaze-related parameter is also referred to as given value of the gaze-related parameter.

For example, the user may be requested to look at a given marker or object displayed at given (desired) position on a screen of and/or mountable to the head-wearable device.

For reasons of accuracy, the scene camera may have a resolution of at least 640×480 pixels or at least 800×600 pixels, more typically of at least 1024×768 pixels, and even more typically of at least 1280×1024 pixels or at least 1920×1080 pixels (at least VGA or even SVGA).

Different to the scene image(s), the resolution of the left and right images is typically comparatively low. The pixel number of the left images and of the typically equally sized right images may be at most 40000, particularly at most 10000, particularly at most 5000, and more particularly at most 2500 or even 1000.

Even with low resolution grayscale left and right images of 64 times 64 pixels, 50 times 50 pixels or even only 32 times 32 pixels a surprisingly high reliability of gaze direction/gaze point prediction can be achieved using trained NNs.

In fact, the gaze direction/gaze point may be accurately detected in many cases even if the left image or the right image or even both images do not contain a pupil or only a portion of the respective pupil.

A right IR-light source of the respective head-wearable device may be used to illuminate the right eye of the respective user and a left IR-light source of the respective head-wearable device may be used to illuminate the left eye of the respective user in embodiments referring to IR-cameras for the left and the right eye, respectively. IR-illumination may only be used/invoked when the image quality is too low or expected to be low, for example in a dark environment. IR-illumination may also be on permanently, or always be on and only switched off to save power and/or when image quality is sufficient without illumination.

Generating or adding the dataset may include concatenating the respective left image and the respective right image. Note that concatenated images may be presented directly to a 2-dimensional input layer of the NN.

Furthermore, generating or adding the respective dataset may include storing a respective representation of a further gaze-related parameter different to the gaze-related parameter, a respective user ID, a respective user-group ID and/or a device ID of the respective head-wearable device. The respective user-group ID may also be part of the user ID.

Storing the respective user ID, the respective user-group ID and/or the device ID of the respective head-wearable device in the datasets of the database may facilitate training the neural network in a device specific, user specific and/or user group specific manner.

For example, the neural network may be trained specifically for children, adults, elderly people, people of a common ethnic origin, women, men, a group of people with common background, a group of people in medication or on a drug, such as alcohol, or visually or otherwise impaired people, a particular device, device class, user ID, user group and the like.

Typically, the database contains respective datasets of a variety of users, states of the users, lighting conditions (indoor and/or outdoor lighting conditions), slippage states of the worn head-wearable device, and/or different distances between the user and a presented object at which the user is gazing.

According to an embodiment of a method for training a neural network, in particular a convolutional neural network, the method includes providing a database having a plurality of datasets each including a respective left image, a respective right image and a respective corresponding representation of a gaze-related parameter, in particular a respective corresponding value of the gaze-related parameter. A neural network having a given architecture is provided. Parameters of the neural network are determined using the respective left images and the respective right images of a sub-set or of all datasets as input and the respective corresponding representations of the gaze-related parameter of the sub-set or of all datasets as desired output of the neural network.

For sake of clarity, the method for training the neural network is also referred to as training method.

According to an embodiment, a trained neural network, i.e. a neural network trained with all or selected datasets of the database, is used to predict a user's gaze-related parameter, in particular a user's eye gaze direction and/or a user's eye gaze point, when the user is wearing a respective head-wearable device, from a left image generated by the first camera and a right image generated by the second camera of the respective head-wearable device, typically in real-time.

As already mentioned above, the training method may be user or user group specific.

Accordingly, a particularly high reliability and/or accuracy of neural network predictions may be achieved for the user or the user group.

Furthermore, the trained neural network may be used to determine a further gaze-related parameter, an ocular parameter and/or a physiological parameter of the user.

For example, the trained neural network may have been trained to detect based on the left and right images if the user is (getting) tired, mentally distracted, and drunken or the like.

Instead of or in addition to using a user specific trained neural network, a calibration method may be used at the user site.

According to an embodiment, a method for calibrating a head-wearable device includes presenting a stimulus to a user wearing the head-wearable device as explained herein. The first camera of the head-wearable device is used to generate a left image of at least a portion of the left eye of the user and the second camera of the head-wearable device is used to generate a right image of at least a portion of the right eye of the user wearing the head-wearable device and being expected to respond to the stimulus or expected to have responded to the stimulus. A trained neural network as explained herein, in particular a trained convolutional neural network, is used to determine a predicted value of the gaze-related parameter using the right image and the left image as an input for the trained neural network. The desired value of the gaze-related parameter and the predicted value of the gaze-related parameter are used to determine a correction function for the user.

The correction function for the user may be stored, locally, for example in a memory of the head-wearable device, and/or within the database.

Differences between corresponding desired and predicted values of the gaze-related parameter may e.g. be due to a specificity of a new user that is not yet sufficiently reflected in the database, a learning error or a change of the user over time.

In any case, the correction function may be used to instantaneously improve the network predictions for the respective user.

On the other hand, the corresponding left and right images and the desired (ground truth) values of the gaze-related parameter may be added as new datasets to the database.

In other words, one or more new datasets having a respective left image, a respective right image, a respective desired gaze-related parameter or another representation of the gaze-related parameter may be generated, and added to the database to generate an updated database.

Accordingly, the updated database covers a larger spectrum of datasets and/or the performance of the retrained network may be improved.

Furthermore, the updated database may be used for retraining the neural network. Accordingly, the performance of the retrained network may be even further improved.

The determined correction function may be used to correct predictions of the trained or retrained NN for the user.

According to an embodiment, the first camera is used to generate a further left image of at least a portion of the left eye of the user and the second camera is used to generate a further right image of at least a portion of the right eye of the user wearing the head-wearable device. The trained or retrained neural network is used to determine a further predicted value of the gaze-related parameter using the further right image and the further left image as an input for the trained neural network. The further predicted value is corrected by applying the correction function to the further predicted value to obtain a corrected value of the gaze-related parameter.

According to a further embodiment, the trained or retrained neural network is used to determine a predicted value of a further gaze-related parameter different to the gaze-related parameter using the right image and the left image as an input for the respective neural network, and the predicted value of the further gaze-related parameter and a desired value of the further gaze-related parameter correlated with the stimulus or a further stimulus is used to determine a further correction function for the user.

The correction function(s) may be implemented as polynomic function(s). For example, a polynomial of two input variables may be used as a correction function for a 2D-gaze direction and a 2D-gaze point, respectively.

Typically, the correction function(s) is/are determined using different pairs of desired and predicted values of the gaze-related parameter(s).

The desired value may correspond to a given value (predetermined value) or a resulting value, and/or may be determined similar as explained above with respect to the method for creating and updating the database.

For example, the above described gaze-related parameter determination unit may be used to determine the resulting value as given value (ground-truth value) of the respective gaze-related parameter, in particular when the user is looking at and/or following his fingertip or another object in his FOV monitored by a scene camera as described herein. Furthermore, the gaze-related parameter determination unit is typically configured to determine a respective given value or resulting value as a respective representation of the gaze-related parameter to be stored in a respective dataset.

In embodiments in which the user is requested to gaze at a given object on a screen, the gaze-related parameter determination unit may, prior to displaying the object, determine the position of the object on the screen in accordance with a given value (predetermined value) of the gaze-related parameter. Alternatively, the gaze-related parameter determination unit may determine the gaze-related parameter in accordance with a randomly chosen position of the object on the screen.

The described calibration method may be at least partly performed and/or controlled by one or more processors of the respective head-wearable device such as a spectacles device as described herein, a goggles, an AR head-wearable display, and a VR head-wearable display, or by one or more processors of a local computer connected with the head-wearable device.

The described calibration method may be invoked when a new user is wearing the head-wearable device for the first time, from time to time, when a slippage of the head-wearable device is likely, expected or detected, or on request of the user.

According to an embodiment, a method for detecting one or more gaze-related parameters of a user includes creating a first image of a left eye of the user using a first camera of a head-wearable device worn by the user, creating a right image of a right eye of the user using a second camera of the head-wearable device, feeding the left and right images together as an input into a (trained) convolutional neural network, and obtaining the one or more gaze-related parameters from the convolutional neural network as a result of the left and right images input.

In the following, the method for detecting one or more gaze-related parameters of the user is also referred to as detection method.

The convolutional neural network is typically a trained neural network as explained herein. Using such a trained convolutional neural network to obtain (determine) respective predicted values of the gaze-related parameter(s) using the right image and the left image as an input allows a particularly high accuracy and reliability of prediction in real time with comparatively low computational resources.

Therefore, the processes of the detection method may be partly or even completely executed by a processing unit or a computer which is integrated in a wearable device, for example in a (standard) spectacle frame of the head wearable device.

Alternatively, the processing unit or the computer may be partly or completely integrated into a desktop computer, a local server, a smart phone, a tablet, or a laptop connected with the head-wearable device.

The left and right images may be concatenated prior to inputting them to the convolutional neural network. Typically, the concatenated images are input in a two-dimensional input layer of the convolutional neural network.

In embodiments referring to equally sized, square-shaped left and right images each having N×N pixels, the input layer is typically a N×2N matrix.

N is typically smaller or equal than 50, preferably smaller or equal than 30, in particular smaller or equal than 20.

In other embodiments, the left and right images are non-quadratic rectangles, but typically also of equal size and shape.

Furthermore, the first and second images may not be pre-processed to obtain spatial and/or temporal patterns or arrangements prior to feeding them to the convolutional neural network. This may further reduce computational costs.

For example, the left and right images may not undergo feature extraction prior to feeding them to the convolutional neural network.

Even further, the output of the convolutional neural network is typically not post processed for obtaining the (predicted values of the) one or more gaze-related parameters.

The predicted value(s) of the gaze-related parameter(s) may be used as input of a further module, e.g. a consumer home related (software) module, a businesses related (software) module and/or a medical related (software) module.

Alternatively, the predicted value(s) are corrected using a user-specific correction function as explained herein prior to using as input for a further module.

For example, the predicted or corrected value(s) may be used by further modules to determine on which object on a screen the user is gazing, how long the user is gazing at the object, if the user is blinking while gazing at the object etc. This information may be used to improve the interaction of the user with a control device or a computer connected with the screen and/or the head-wearable device or for advertising.

In embodiments referring to a head-wearable device having a display, the display of the head-wearable device may act as the screen.

The convolutional neural network has typically at least 6 layers, and preferably more than 10 layers.

The convolutional neural network may have between 12 and 30 layers, preferably between 16 and 20 layers.

The convolutional neural network typically uses a filter kernel or filter kernels of size M, with M being in the range from 1 to 7, preferably 3 to 5.

Note that filter kernel sizes are often given as a single integer number M. This means that the matrix of the filter is in fact sized M×M×Nc, where Nc is the number of channels in the corresponding layer of the network.

For example, if left and right RGB color images (3 channels) are used as input, then the first convolutional layer may have for M=5 exemplary 16 filter matrices or kernels of 5×5×3 size, resulting in the next layer of data with 16 channels, namely one from each of the convolution with one of the sixteen 5×5×3 filters of the previous layer. Likewise, if left and right grayscale images (1 channel) are used as input, then the respective filter matrices or kernels for M=5 would have a size of 5×5(×1).

Any of the head-wearable devices described herein may be used for detecting one or more gaze-related parameters.

In one embodiment, the first and second cameras may be located within a range of 32 to 40, preferably, 34 to 38, in particular 36, degrees with respect to the median plane of the head-wearable device.

In another embodiment, the first and second cameras are located within a range of 114 to 122 degrees, preferably 116 to 120, preferably 118, with respect to the median plane of the head-wearable device.

In both embodiments, the typically tiny cameras are not even noticed by the user when wearing the device.

For example, the first and second cameras may have respective volumes of less than about 40 mm$^3$ or even 10 mm$^3$.

The head-wearable device may be part of a system capable of improving the parameter prediction of users over time.

According to an embodiment, a system for improving the prediction of gaze-related parameters includes at least one head-mountable device, a processing unit and a computing system. The computing system is connectable with the processing unit, and configured to host a first database and to train the neural network, in particular a convolutional neural network, using the first database. The at least one head-mountable device includes a first camera for generating a left image of at least a portion of a left eye of a user and a second camera to generate a right image of at least a portion of a right eye of the user when the user is wearing the head-mountable device. The processing unit is connectable with the first camera and the second camera, and configured to determine a predicted value of a gaze-related parameter of the user using the left image and the right image as input of the neural network. The system is configured to add datasets to the first database and to transfer parameters of the neural network (or even a complete model of the NN) from the computing system to the processing unit. The added datasets include a respective left image, a respective right image and a respective representation of the gaze-related parameter of the user.

Typically, the system includes a plurality of head-mountable devices as explained herein.

Accordingly, datasets of many users can contribute to update the database and thus to improve (via training or retraining using the database) the neural network transferred to and used for predicting the gaze-related parameter(s) at the user site.

In an exemplary embodiment, a gaze-related parameter determination unit of the respective head-wearable device is used to determine a given or resulting gaze direction of the user and/or a given or resulting gaze point as the desired value of the respective gaze-related parameter.

The gaze-related parameter determination unit may include a scene camera arranged to capture a field of view of the user wearing the respective head-wearable device.

Note that not only the instance but also the implementation of the NN in the training phase (in the computing system) and the running phase (at the user site) can differ.

Reference will now be made in detail to various embodiments, one or more examples of which are illustrated in the figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appended claims. The drawings are not scaled and are for illustrative purposes only. For clarity, the same elements or manufacturing steps have been designated by the same references in the different drawings if not stated otherwise.

With reference to FIG. 1A to 1C, a generalised embodiment of a head-wearable spectacles device for determining one or more gaze-related parameters of a user is shown. In fact, with the help of FIGS. 1A and 1C a plurality of embodiments shall be represented, wherein said embodiments mainly differ from each other in the position of the cameras 14, 24. Thus, the spectacles device 1 is depicted in FIG. 1A with more than one camera 14, 24 per ocular opening 11, 21 only for presenting each embodiment. However, in this embodiment the spectacles device does not comprise more than one camera 14, 24 associated to each ocular opening 11, 21.

FIG. 1A is a view from above on said spectacles device 1, wherein the left side 10 of the spectacles device 1 is shown on the right side of the drawing sheet of FIG. 1A and the right side 20 of the spectacles device 1 is depicted on the left side of the drawing sheet of FIG. 1A. The spectacles device 1 has a middle plane 100, which coincides with a median plane of the user of the spectacles device 1 when worn according to the intended use of the spectacles device 1. With regard to user's intended use of the spectacles device 1, a horizontal direction 101, a vertical direction 102, 100, a direction "up" 104, a direction "down" 103, direction towards the front 105 and a direction towards the back 106 are defined.

The spectacles device 1 as depicted in FIG. 1A, FIG. 1B, and FIG. 1C comprises a spectacles body 2 having a frame 4, a left holder 13 and a right holder 23. Furthermore, the spectacles body 2 delimits a left ocular opening 11 and a right ocular opening 21, which serve the purpose of providing an optical window for the user to look through, similar to a frame or a body of normal glasses. A nose bridge portion 3 of the spectacles body 2 is arranged between the ocular openings 11, 21. With the help of the left and the right holder 13, 23 and support elements of the nose bridge portion 3 the spectacles device 1 can be supported by ears and a nose of the user.

According to the embodiments represented by FIG. 1A, a left camera 14 and a right camera 24 can be arranged in the spectacles body 2. Generally, the nose bridge portion 3 or a lateral portion 12 and/or 22 of the spectacles body 2 is a preferred location for arranging/integrating a camera 14, 24, in particular a micro-camera.

The specific location of the respective camera 14, 24 can be provided by defining an angle of an optical axis 15, 25 of the respective camera 14, 24 with respect to the middle plane 100.

If a camera 14 or 24 is arranged in the nose bridge portion 3 of the spectacles body 2, the optical axis 15 of the left camera 14 is inclined with an angle α of 142 to 150°, preferred 144°, measured in counter-clockwise direction (or −30° to −38°, preferred −36°) with respect to the middle plane 100. Accordingly, the optical axis 25 of the right camera 24 has an angle β of inclination of 30° to 38°, preferred 36°, with respect to the middle plane 100.

If a position of a camera 14, 24 is located in one of the lateral portions 12, 22 of the spectacles body 2, the optical axis 15 of the left camera 14 has an angle γ of 55 to 70°, preferred 62° with respect to the middle plane, and/or the optical axis 25 of the right camera 24 is inclined about an angle δ of 125° to 110° (or −55° to −70°), preferred 118° (or −62°).

The spectacles device 1 of FIG. 1A stands for various embodiments, having different positions of the cameras 12, 24, for example that both cameras 14, 24 are located in the nose bridge portion 3, the left camera 14 is placed in the left lateral portion 12 and the right camera 24 is located in the right lateral portion 22, or that the left/right camera 14/24 is arranged in the nose bridge portion 3 and the right/left camera 24/14 is arranged in the right/left lateral portion 22/12.

In order to provide an additional or alternative specification for a location of a camera 14, 24 in the spectacles body 2, specific camera placement zones 17, 18, 27, 28 are defined, wherein a related technical teaching is in line with the upper specification using angles α, β, γ, δ of the optical axis 15, 25. Said camera placement zones 17, 27, 18, 28 are virtual areas projected in a vertical plane being perpendicular to the middle plane 100.

Furthermore, a bounding cuboid 30—in particular a rectangular cuboid—can be defined by the optical openings 11, 21, which serves four specifying positions of the camera placement zones 17, 27, 18, 28. As shown in FIG. 1A, FIG. 1B, and FIG. 1C the bounding cuboid 30—represented by a dashed line—includes a volume of both ocular openings 11, 21 and touches the left ocular opening 11 with a left lateral surface 31 from the left side 10, the right ocular opening 21 with a right lateral surface 32 from the right side 20, at least one of the ocular openings 11, 21 with an upper surface 33 from above and from below with a lower surface 34.

In case a left/right camera 14, 24 is arranged in the nose bridge portion 3, a projected position of the left camera 14 would be set in a left inner eye camera placement zone 17 and the right camera 24 would be (projected) in the right inner eye camera placement zone 27.

When being in the left/right lateral portion 12, 22, the left camera 14 is positioned—when projected in the plane of the camera placement zones—in the left outer eye camera placement zone 18, and the right camera 24 is in the right outer eye camera placement zone 28.

With the help of the front view on the spectacles device 1 depicted in FIG. 1B the positions of the eye camera placement zones 17, 18, 27, 28 are explained. In FIG. 1B rectangular squares represent said eye camera placement zones 17, 18, 27, 28 in a vertical plane perpendicular to the middle plane 100. Both inner eye camera placement zones 17, 27 start at a distance of 2 mm from the middle plane 100 to a distance of 14 mm in horizontal direction 101 towards the left/right direction.

In a vertical direction 102 the inner eye camera placement zones 17, 27 stretch out for 22 mm, beginning in a distance of 9 mm from the upper surface 33 down to a distance of 31 mm. Thus, the inner eye camera placement zones 17, 27 have a size of 12 mm in horizontal direction 101 and 22 mm in vertical direction 102.

The left and right outer eye camera placement zones 18, 28 are recently referenced to the respective left and right lateral surface 31, 32 of the bounding cuboid 30. Doing so, the respective outer eye camera placement zone 18, 28 starts in direction towards the middle plane 100 from a distance of 5 mm from the respective lateral surface 31, 32 and extents from there in opposite direction, away from the middle plane 100, up to a distance of 6 mm from the respective lateral surface 31, 32. Therefore, the respective lateral surface 31, 32 intersects with the respective outer eye camera placement zone 18, 28.

The size of the outer eye camera placement zones 18, 28 in vertical direction is preferably 28 mm to 30 mm.

As a preferred option, all embodiments of the spectacles device 1 as represented by FIG. 1A to 1C have in common, that no more than one camera 14/24 is associated to one of the optical openings 11, 21; hence the spectacles device 1 does only comprise two cameras 14, 24 to take a picture of a left and a right eyeball 19, 29.

The spectacles device 100 as shown in FIG. 1A comprises a processing unit 7 configured for processing the left and the right picture from the respective camera 14, 24 for determining the gaze-related parameter using at least one convolutional neuronal network. According to the present embodiments, the processing unit 7 is non-visibly integrated within the holder, for example within the right holder 23 or the left holder 13 of the spectacles device 1. According to a non-shown embodiment, a processing unit can be located within the left holder.

With reference to FIG. 2A, embodiments of a method 1000 for creating and updating a database are explained. The database is typically used for training a neural network, in particular a convolutional neural network. This is explained below with regard to FIG. 3A in more detail.

In a first block 1100, a first stimulus S is presented to a user wearing a head-wearable device. The head-wearable device may be any of the head-wearable devices described herein. It may be implemented as a spectacles device, e.g. a glasses, a goggles, an AR head-wearable display, and a VR head-wearable display. The head-wearable device has a first camera arranged next to a left eye of the user and a second camera arranged next to a right eye of the user when the first user is wearing the head-wearable device.

The database may be used for training the neural network to predict the user's gaze-related parameter, in particular a user's eye gaze direction and/or a user's eye gaze point, when the user is wearing the head-wearable device, from a pair of a left image generated by the first camera and a right image generated by the second camera as input of the neural network.

Accordingly, the database may include a plurality of datasets including pairs of left and right images and one or more corresponding values of gaze-related parameters considered to be respective actual values or ground truth values.

The database may be user specific.

More typically, the database includes datasets of a plurality of users, i.e. of a first user, a second user, a third users, a fourth user and so on and so forth. For sake of clarity, the following description is mainly given for an exemplary user or first user.

Using datasets of a plurality of users for training the neural networks may enhance learning (generalization) and thus improve the accuracy and/or liability of the predictions of the NN.

Likewise, the database typically includes datasets obtained using several head-wearable device which are typically of the same type. At least the positions and alignments of the left and right camera of the head-wearable devices are typically at least substantially equal. Alternatively, the positions and alignments of the left and right camera of the head-wearable devices are also stored (coded) in the datasets and used as inputs for training the neural network.

In a subsequent block 1200, the first and second cameras of the head-wearable device record a respective image $P_l$, $P_r$, typically a respective photo, of the users left and right eye when the user is expected to respond to the first stimulus or expected to have responded to the first stimulus. The image $P_l$, $P_r$ may also be selected from a respective video stream or image sequence recorded using the first and second cameras.

In a subsequent block 1500, a dataset consisting of or including the left image $P_l$, the right image $P_r$ and a representation of a (desired) gaze-related parameter is saved (stored) in the data base. The representation of the gaze-related parameter may be a given or determined respective (ground truth) value of the gaze-related parameter, but also any other representation such as a corresponding image of a scene camera that is correlated with the first stimulus and suitable for determining the (ground truth) value of the gaze-related parameter.

In one embodiment, the user wearing the head-wearable device is requested in block 1100 by an acoustic stimulus, a visual stimulus or a combination or sequence of acoustic and visual stimuli, to look at (gaze at) a given object in his field of view (FOV). The given object may be a real object in the user's FOV such as a finger tip of the user, an object in the room, or an object displayed on a screen of the head-wearable device.

The size of the given object should be sufficiently small and well defined in order to provide an unambiguous gaze target.

Accordingly, the co-ordinates and the direction of the given object in a co-ordinate system fixed with the head-wearable device and thus with the user's head is well enough defined to be considered as actual (or ground truth) values of the gaze point and gaze direction, respectively, of the user wearing the head-wearable device.

Cooperative behaviour of the user can be assumed, as the user has an interest in improving the accuracy and robustness of the predictions of the trained NN, i.e. a NN which is trained using and thus depending on the quality of the datasets in the database.

In one embodiment, more than one gaze-related parameter, for example two or three gaze-related parameters are added with the dataset to the database in block 1500.

For example, instead or in addition to actual values or other representations of a cyclopean gaze direction, values or other representations of respective gaze directions of one or both eyes, of pupil axis orientations of one or both eyes, of a 3D gaze point, or of a 2D gaze point may be added with the dataset to the database in block 1500.

As indicated by the left and right dashed arrows in FIG. 2A, the method 1000 may return to block 1100 for presenting a further stimulus or even the same stimulus again. Note that several datasets may be added in block 1500.

Presenting the same stimulus may be useful for statistical reasons, to obtain datasets under different conditions, for example for a fresh and a tired user or at different times and/or light conditions.

Furthermore, the stimulus may not be one-to-one related with the resulting value of the gaze-related parameter(s).

For example, the user may hold the finger in different positions with respect to the device defined co-ordinate system when requested to gaze at a tip of one of his fingers held in his FOV. Although the fingertip defines inter alia a respective resulting gaze direction relative to the co-ordinate system fixed with the head-wearable device, the actual value of the resulting gaze direction to be stored in the database may yet have to be determined. In these embodiments, a gaze-related parameter determination unit, for example a gaze-related parameter determination unit including a scene camera arranged to capture the given object in the field of view of the user, typically a scene camera of the head-wearable device, may be used to determine an actual value of the gaze-related parameter, for example a resulting gaze direction and/or the respective resulting gaze point of the user.

Based on the image(s) of the scene camera, the actual value(s) of the gaze-related parameter may be determined using known machine learning, computer vision or image processing techniques. This may be done locally, i.e. using one or more processors of a processing unit of the head-wearable device or of a typically more powerful local computer connected with the head-wearable device or using one or more processors of a typically even more powerful computing system also hosting the database. In the latter case, the dataset(s) may include the image(s) of the scene camera as representations of the gaze-related parameter(s).

For sake of clarity, the following description focuses on the (2D or 3D) gaze direction and the (2D or 3D) gaze point (determined in the co-ordinate system fixed with the head-wearable device) as gaze-related parameters. This is however to be understood as not limiting. The skilled user appreciates that other gaze-related parameters may be handled likewise. For example, the system may be used to assess cognitive load. Relative changes of pupil diameters as reflected in recorded images can be linked to some kind of cognitive load measure. Cognitive load itself may be determined via an additional device, such as an EEG, which serves as the label (ground truth). The dataset then consists of the respective images and said cognitive load measure.

Figure 2C:
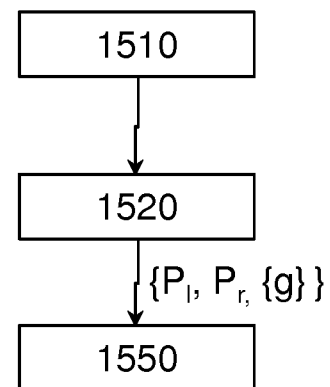
FIG. 2C illustrates a flow chart of a portion of the method shown in FIG. 2A and FIG. 2B, respectively according to embodiments.
Figure 2B:
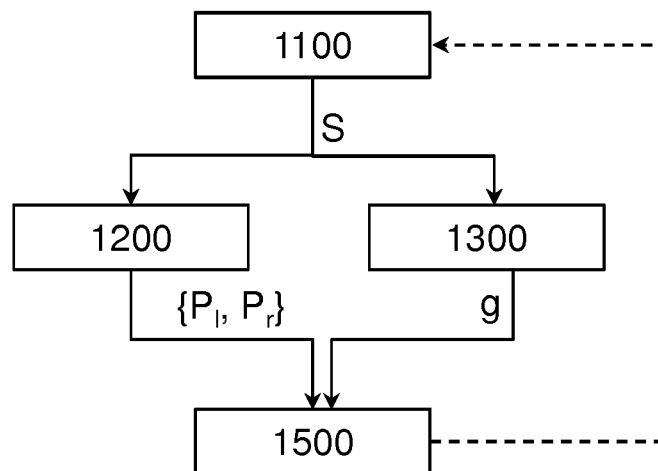
FIG. 2B illustrates a flow chart of a method for creating and updating a database for training a neural network according to embodiments.

Using a gaze-related parameter detection or determination unit of the head-wearable device for determining the actual value g of the gaze-related parameter is represented by a block 1300 in FIG. 2B illustrating a method 1001 which is apart from block 1300 typically similar to the method 1000.

In embodiments in which a screen of the head-wearable device is used for displaying objects for the user as stimuli, the actual value(s) g of the gaze-related parameter is typically known or given.

For example, the gaze point and/or the gaze direction of the object may, for a given head-wearable device, be calculated from the coordinates of the object on the screen. Alternatively, the gaze point and/or the gaze direction may be given in the co-ordinates of the co-ordinate system fixed with the head-wearable device and the screen, respectively, and the desired (2D) co-ordinates of the displayed object on the screen may be calculated prior to displaying the object on the screen.

With regard to FIG. 2C, an embodiment of the block 1500 as used in methods 1000 and 1001 is explained in more detail.

In a first sub-block 1510, a data connection is established between the head-wearable device and the database.

Thereafter or prior to block 1510, one or more dataset $\{P_l, P_r, \{g\}\}$ are generated in sub-block 1520. Each dataset may have a respective left image, a respective right image and a respective representation of one or more gaze-related parameters $\{g\}$ and correlated with a respective stimulus S.

In subsequent sub-block 1550, the one or more datasets $\{P_1, P_r, \{g\}\}$ are added to the database.

The datasets may include the pairs of left and right images as a respective concatenated image. Concatenated images can be presented to a 2-dimensional input layer of the NN. Accordingly, the pairs of left and right images may be typically concatenated in block 1520.

Different to the scene image(s), the resolution of the left and right images may be comparatively low. The pixel number of the left images and of the typically equally sized right images may be at most 10000, particularly at most 5000, and more particularly at most 2500 or less.

Even with low resolution grayscale left and right images of 64 times 64 pixels, 50 times 50 pixels or even only 32 times 32 pixels or only 24 times 24 pixels a surprisingly high accuracy (for example lower than 2° mean angular prediction error) and reliability of prediction gaze directions and/or gaze points can be achieved using trained CNNs.

Figure 3A:
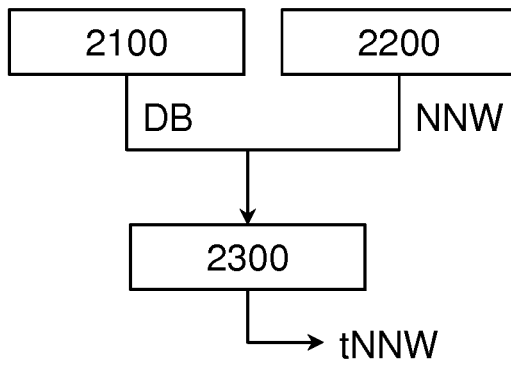
FIG. 3A illustrates a flow chart of a method for training a neural network according to embodiments.

With regard to FIG. 3A, a method 2000 for training a neural network is explained.

In block 2100, a database DB created and/or updated as explained above with regard to FIGS. 2A to 2C is provided. The database DB has a plurality of datasets each having a respective left image, a respective right image and a respective corresponding representation of a gaze-related parameter, e.g. a respective corresponding value of the gaze-related parameter.

Further, a neural network NNW with a given network architecture is provided in a block 2200. The provided neural network NNW is typically a convolutional NN.

The provided neural network NNW may be a previously trained NN.

Alternatively, the parameters (weights) of the provided neural network NNW may have been initialized with random values.

In block 2300, parameters of the neural network are amended using the respective left images and the respective right images of a sub-set or of all datasets as input and the respective corresponding representations of the gaze-related parameter of the sub-set or of all datasets as desired output of the neural network.

Block 2300 may include many teaching cycles each of which uses one or more datasets of the database DB.

Typically, a deep learning technique, in particular a gradient descent technique such as backpropagation may be used to train the neural network NNW in block 2300.

Finally, a trained or retrained neural network tNNW may be output and/or stored.

In particular, the determined weights of tNNW may be stored and typically later transferred to a processing unit of or connectable with a head-wearable device.

More typically, the determined weights of tNNW are (later) transferred to a plurality of respective processing units and/or head-wearable devices.

Thereafter, one or more local instances of the trained neural network tNNW may be used to predict gaze-related parameter(s) of a respective user, when the user is wearing a head-wearable device, from left and right images generated by the respective cameras of the head-wearable device, typically in real-time.

Figure 3C:
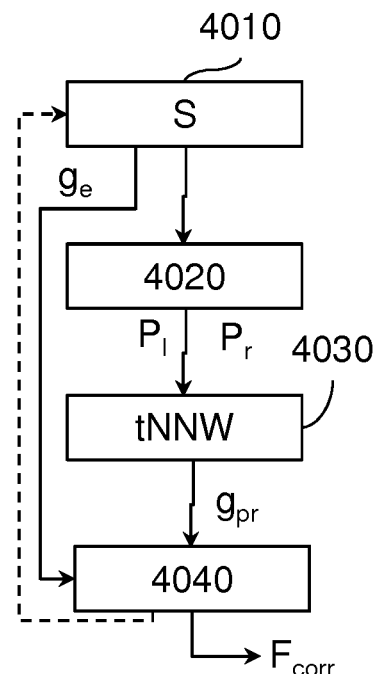
FIG. 3C illustrates a flow chart of a method for detecting one or more gaze-related parameters according to embodiments.
Figure 3B:
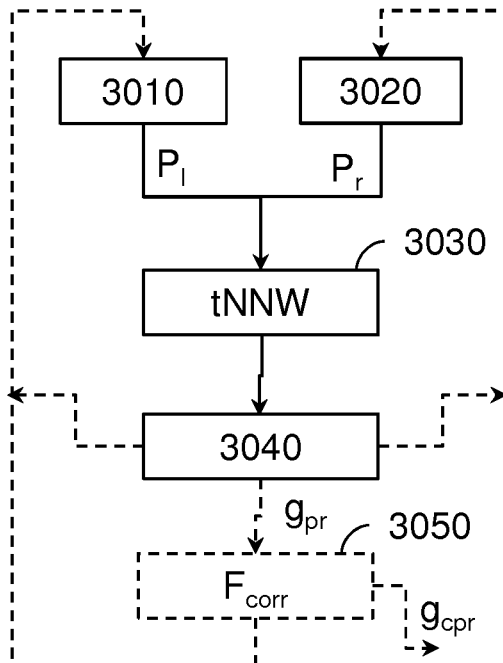
FIG. 3B illustrates a flow chart of a method for calibrating a head-wearable device.

As shown in FIG. 3B illustrating a detection method 3000, a left image $P_l$ of at least a portion of a left eye of the user may be taken by a first camera of a head-wearable device worn by the user, and a right image $P_r$ of at least a portion of a right eye of the user may be taken by second camera of the head-wearable device in blocks 3010, 3020.

The left image $P_1$ and the left image P are typically taken at substantially the same time.

In a subsequent block 3030, the left image $P_l$ and the right image $P_r$ may be fed together as an input into a trained convolutional neural network tNNW, typically as a concatenated image to an input layer of the trained convolutional neural network tNNW.

In a subsequent block 3040, a predicted value $g_{pr}$ of one or more gaze-related parameters may be obtained from the trained convolutional neural network tNNW as a result of the left and right images input, typically as output of an output layer of the trained convolutional neural network tNNW.

The predicted value(s) $g_{pr}$ may be corrected using a user specific correction function $F_{corr}$ in an optional block 3050.

The predicted value(s) $g_{pr}$ or the corrected predicted value(s) $g_{cpr}$ may be output and/or used as input for an evaluation module, e.g. a user interface module using gaze-related user parameters.

After leaving block 3040 or block 3050, method 3000 may return to the blocks 3010, 3020 as indicated by the dashed arrows.

With regard to FIG. 3C, an embodiment of a method 4000 for calibrating a head-wearable device is explained.

In a block 4010, a stimulus S is presented to a user wearing the head-wearable device. The stimulus S is correlated with a desired (expected) value $g_e$ of a gaze-related parameter.

In a subsequent block 4020, the first camera and second camera of the head-wearable device are used to take a left image $P_l$ of at least a portion of the left eye of the user and a right image $P_r$ of at least a portion of the right eye of the user expected to respond (have responded) to the stimulus S.

Thereafter, a trained neural network tNNW, in particular a trained convolutional neural network, is used to determine a predicted value $g_{pr}$ of the gaze-related parameter using the right and left images $P_1$, $P_r$ as an input for the trained neural network tNNW in a block 4030.

In a subsequent block 4040, a difference between the desired value $g_e$ and the predicted value $g_{pr}$ may be calculated and used to determine a correction function $F_{corr}$ for the user.

As indicated by the dashed arrow in FIG. 3C, the correction function $F_c r$ is typically determined after several cycles.

Figure 3D:
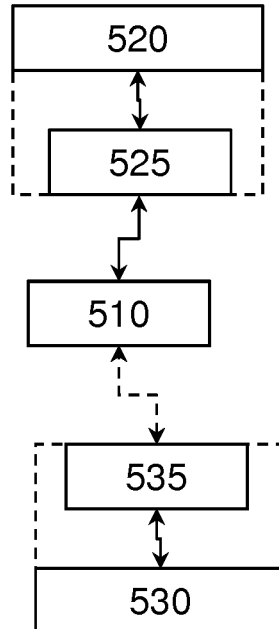
FIG. 3D illustrates a system for improving the prediction of gaze-related parameters according to an embodiment.

With regard to FIG. 3D, an embodiment of a system 500 for improving the prediction of gaze-related parameters is explained.

The system 500 has a computing system 510 hosting a database as explained herein. The computing system 510 may be implemented as/operate as or include a server for hosting the database. The computing system 510 may consist of a single or a plurality of connected computers.

The computing system 510 is configured to train a neural network using the database. For this purpose, the computing system 510 may have one or more hardware components which are particularly suited for realizing and training NNs, in particular CNNs such as GPUs.

In the exemplary embodiment, the computing system 510 is connected with a processing unit 525 connectable with or even forming a part of a head-mountable device 520 having a first camera for generating a left image of at least portion of a left eye of a user and a second camera for generating a right image of at least portion of a right eye of the user when the user is wearing the head-mountable device.

When connected with left and right cameras, the processing unit 525 is configured to receive the left and right images.

In addition, the processing unit 525 is configured to determine a predicted value of a gaze-related parameter of the user using the left image and the right image as input of a neural network instance, in particular a convolutional neural network instance when running in the processing unit.

The processing unit 525 typically also has one or more hardware components which are particularly suited for running NNs, in particular CNNs such as a GPU.

The processing unit 525 is typically configured to control and/or to execute the method 3000 explained above with regard to FIG. 3B.

Furthermore, the processing unit 525 is typically configured to control and/or to execute the method 4000 explained above with regard to FIG. 3C.

In the illustrated connected state, the processing unit 525 and the computing system 510 are configured to transfer datasets from the processing unit 525 to the computing system 510, to add datasets to the database, and to transfer parameters of the neural network from the computing system 510 to the processing unit 525.

The computing system 510 is typically connected with one or more further processing units 535 connected with or even forming a part of a respective further head-mountable device 530 each having a respective first camera and respective second camera.

The processing unit 525 may be operable as a client when connected with the computing system 510 operating as server.

Client(s) and server are typically remote from each other and typically interact through a communication network such as a TCP/IP data network. The client—server relationship arises by virtue of software running on the respective devices.

Typically, the communication between the processing unit 525 and the computing system 510 uses encryption.

The system 500 is at least in a connected state capable to execute any of the methods explained herein, in particular the methods 1000 to 4000.

Furthermore, the system 500 is typically also configured to execute any of the processes explained in the following.

Figure 4:
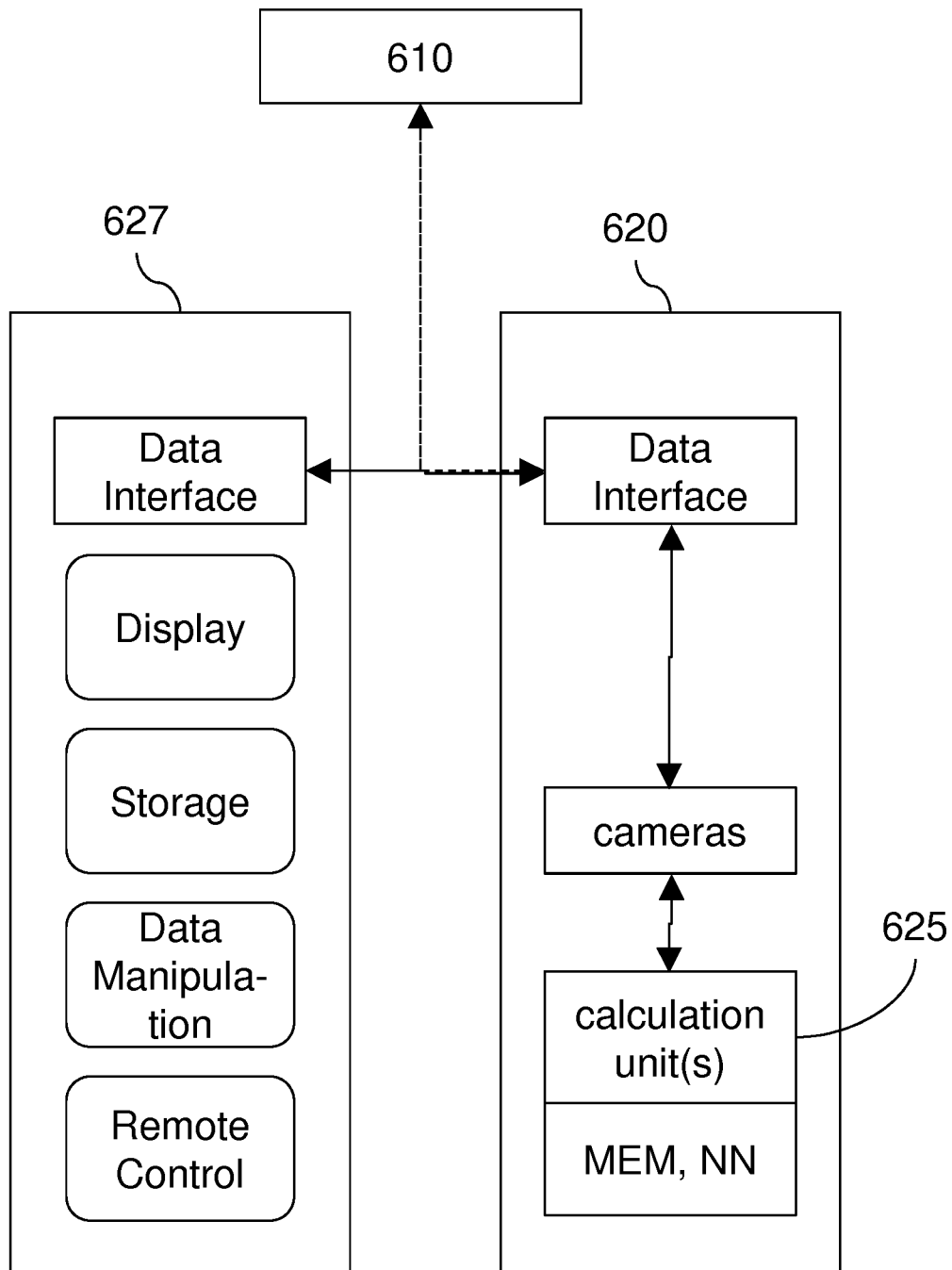
FIG. 4 illustrates a system for improving the prediction of gaze-related parameters according to an embodiment.

With regard to FIG. 4 an embodiment of a system 600 for improving the prediction of gaze-related parameters is explained. The system 600 is similar to the system 500 explained above with regard to FIG. 3D and also includes a computing system 610. For sake of clarity, only one head wearable device 620 is shown in FIG. 4.

In the exemplary embodiment, the head wearable device 620 can connect to an exemplary companion device, such as a tablet or smartphone 627 for control, power supply and (intermediate) storage of generated datasets. The companion smartphone 627 can also be used to upload collected labelled datasets to the computing system 610 hosting the database, download (update) a used (convolutional) neural network when desired, as will be described in further detail with reference to FIGS. 5 and 6, and to interact with the user. The communication connection between the smartphone 627 and the head wearable device 620 can be a magnetically attached USB 2.0 (or above) cable which exits the frame behind the left or right ear of the wearer and connects to the phone's USB-C port.

A companion app, i.e. a computer program designed to run on a mobile device such as a phone/tablet or watch (mobile app), running on the companion smartphone 627 can be the primary user interaction point. The user may be able to control recordings, user profiles, calibrations and validations via the companion app. The user may also be able to update and manage personal profiles, network models, and calibrations with the app. Such interactions may be low or minimal. The smartphone 627 is typically able to operate autonomously in a fully automated fashion. The companion app may control the device and may send firmware and model updates.

The head wearable device 620 may also include components that allow determining the device orientation in 3D space, accelerometers, GPS functionality and the like.

The head wearable device 620 may further include any kind of power source, such as a replaceable or rechargeable battery, or a solar cell.

According to an embodiment, the computation of the user's gaze point is done by a processing unit or controller 625 being fully and invisibly integrated into a standard spectacle frame of the device 620, one example of which is the Intel/Movidius Myriad2 VPU with CNN-inference capabilities. In this case, a trained CNN model may be loaded via the companion 627 and run on the integrated controller 625.

The controller 625 can receive respective images from the left and right eye cameras of the device 620, run inference using the trained CNN and sends the predicted gaze position data (or predicted values of other gaze-related parameters) to the connected companion smartphone 627 for display and storage.

The controller 625 may also forward the input image data from the eye cameras when requested, for example for data collection and/or use in a "refinery", as will be described below with reference to FIGS. 5 and 6.

The controller 625 may also send the images of a scene camera of the device 620 to the companion smartphone for display and storage. The latter function may be achieved by a separate special purpose controller that uses the same USB connection.

Alternatively, an on-device controller of the device 620 only controls the cameras and forwards the image data to the companion device 627 or even more remotely such as to the computing system 610, for example a remote server and/or cloud based structure or the like without doing any inference of the ocular parameter(s) on the user site.

Within the companion smartphone 620 one or more DSPs, one or more special purpose chips, and/or one or more GPUs may be used for gaze estimation using CNN based inference.

Irrespective of which device performs the task of determining the ocular parameter(s), the user may have access to gaze data and scene videos in real time for their use cases. The companion phone 627 or another mobile device can also act as a relay and allow the user to upload their recorded data to a destination of their choosing as well as upload the labeled training data to a server or servers, as will be described in the following.

Figure 5:
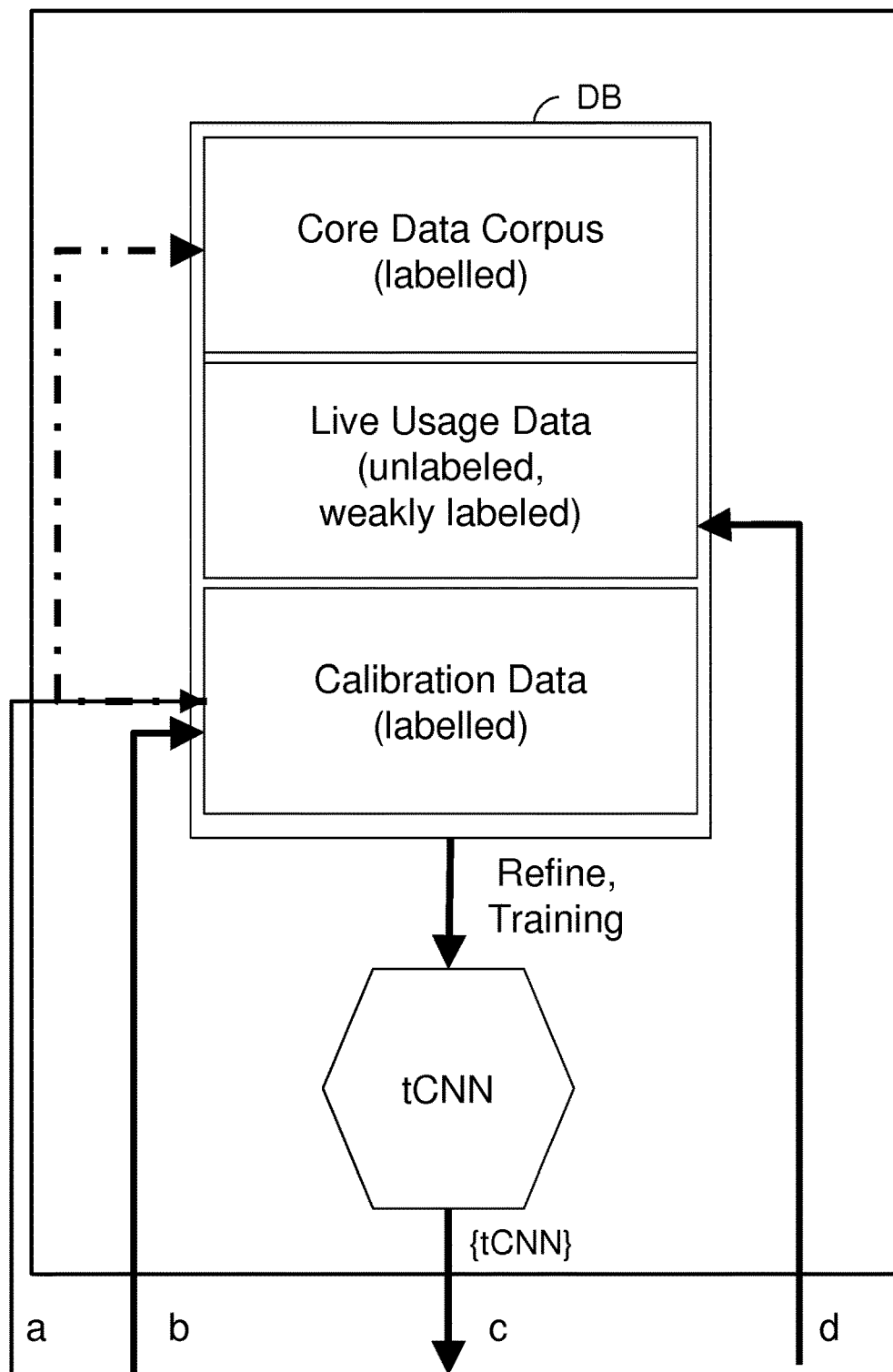
FIG. 5 illustrates a system for improving the prediction of gaze-related parameters according to an embodiment.
Figure 6:
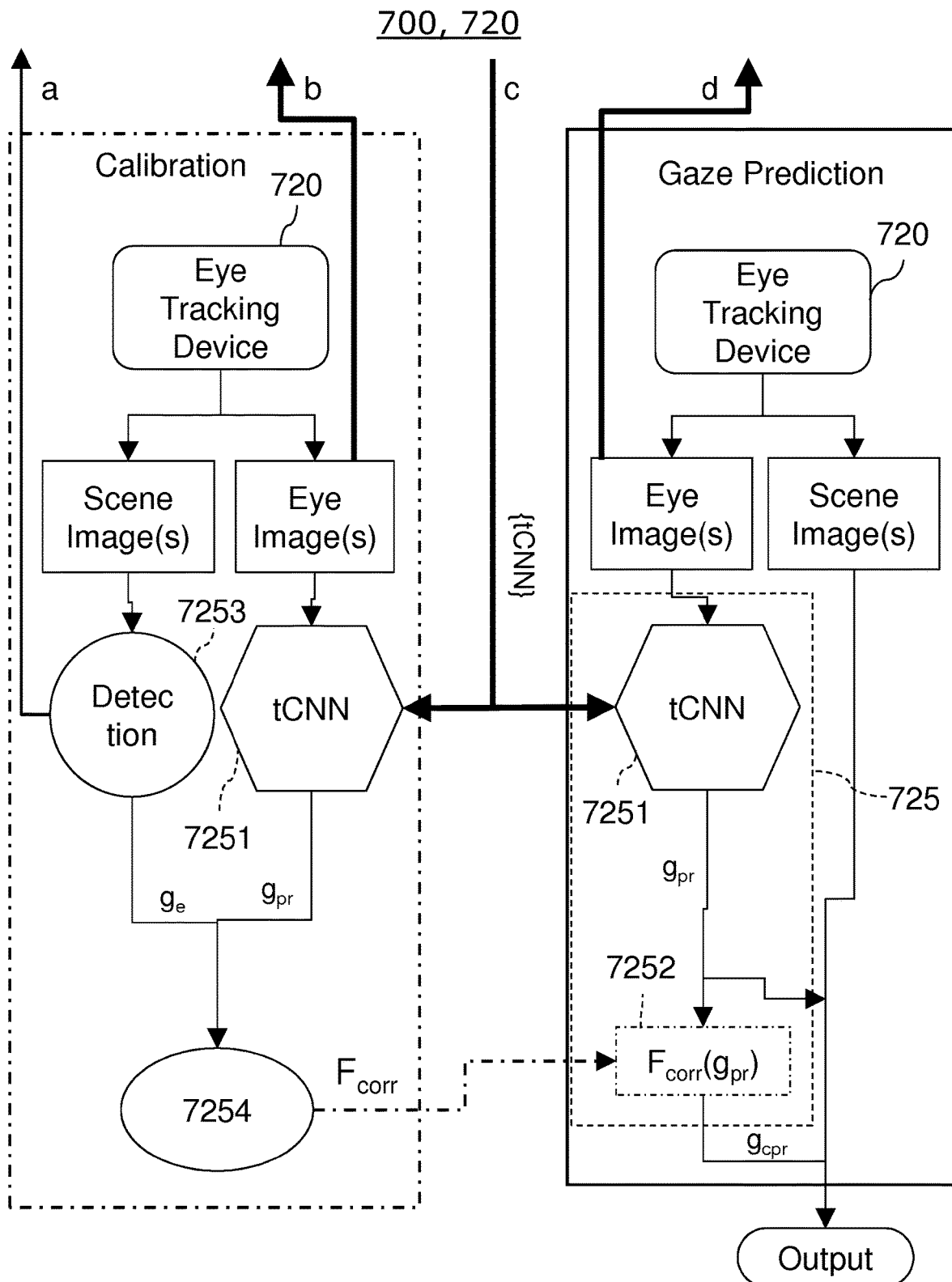
FIG. 6 illustrates a system for improving the prediction of gaze-related parameters according to an embodiment.

With regard to the FIGS. 5 and 6, embodiments of a system 700 for improving the prediction of gaze-related parameters are explained. The system 700 is typically similar to the system 500 and 600 explained above with regard to FIGS. 3D and 4, respectively, and also includes a computing system 710.

For sake of clarity, the system 700 and its operation is shown in the two FIGS. 5 and 6. FIG. 5 refers to the computing system 710. FIG. 6 refers to a head-wearable device 720 of the system 700 connectable with the computing system 710 (see also the arrows a-d representing flow of information).

One task of the present disclosure is to generate, provide, apply, and improve a so-called "universal neural network" (also referred to as universal NN-model and "cross-user NN-model") for determining ocular parameters, in particular gaze direction information of users. Such a universal NN is in its basic embodiment suitable for application as is, without any further calibration or setup steps by a "new" user, meaning a user whose datasets have not been used to train the NN.

It is thus assumed, that a so-called core data corpus of labelled datasets has been collected and stored in a database DB and a learning algorithm based on NNs has been trained based on said data.

The core data corpus can for example consist of datasets of image pairs picturing (respective portions of) the left and right eye and corresponding ground truth gaze points in scene camera image coordinates.

The core data corpus typically covers a large variety of naturally occurring appearances of the eyes. Thus, while recording training data special care may be taken to cover the entirety of possible appearance ranges of the eye images. This way it is made sure that the universal NN will work robustly on all images occurring in practice.

Factors that for example may be covered are different lighting conditions (in particular also outdoor lighting conditions), different poses of the headset (head-mountable device) on the user's head (to reflect headset slippage), differences in the physiological appearance of the user induced by for example gender or affiliation with an ethnic group, short-term physiological changes (e.g. on one day a user's eyes are more swollen or widely opened compared to another) and distance between gaze target and user as will be described in the following (different gaze distances lead to different levels of vergence of the eyes). Furthermore, the ground truth gaze points should correspond to objects at different distances from the user, to ensure that also a variety of different states of binocular vergence is present in the data corpus.

In addition, data augmentation methods may be used in order to further diversify the core data corpus and increase the amount of available data.

To further augment the amount of slippage configurations of the headset on a given user, slippage simulation has been found to be beneficial. Given a pair of eye images of the left and right eye together with the ground truth gaze label for that pair, samples of random movements which the headset might undergo due to slippage are generated. Given these movements and the fixed geometric relations between all cameras in the headset, projective transformations that produce the effect implied by the movements can be calculated. This way, valid additional samples of labelled datasets can be calculated without having to actually record them.

Similarly, random erasing in which randomly chosen regions in an image are erased and the corresponding pixels replaced with random values or a mean image pixel value produces images with various levels of simulated occlusion which can serve as additional "artificial" training datasets, which comes at no additional cost but adds to the diversity of the core data corpus.

A universal NN trained on such a core data corpus has then learned to produce or predict an output which encodes an ocular parameter, such as the gaze direction of any user. In one possible example, the output is given as 2D pixel coordinates of the gaze point in the scene camera image. Other encodings like for example the 3D location of the gaze point in some 3D coordinate system; or the 3D gaze ray in eye camera coordinates can be implemented as well.

In preferred embodiment, the system 700 is binocular, i.e. its cameras capture (the state of) both eyes. A binocular capture is important (necessary in most cases) to determine the exact location of the gaze point, which can only be inferred from the binocular vergence of the eyes. With a monocular system one can only infer the 3D gaze direction of the user, but one cannot infer the precise depth of the gaze point. Given the 3D gaze direction one could also compute the exact gaze location by intersecting the gaze ray with the world geometry, assuming this geometry is known.

As to the NN model to be trained for use in the system and methods of the present disclosure, it has been surprisingly found that Convolutional Neural Networks (CNNs) are able to yield sufficient accuracy, despite the inherently challenging mobile respectively wearable setup of the device, which leads to low resolution of the input images and the challenging viewpoint of the unobtrusively placed optical sensor(s).

While CNNs have been used for tasks like object recognition where this can be beneficial, their use in end-to-end gaze prediction in a mobile setting has not previously been attempted. Given the great variety in image appearance in such a setting, leading to images which do not even always show the pupil or only show small fractions of the pupil, with large variations in lighting conditions and skin tone, it is unexpected that CNNs should be trainable to learn sufficiently meaningful convolution kernels to provide a universal cross-user model for accurate gaze prediction based on merely two low resolution input images.

By exploiting the use of CNNs in a mobile respectively wearable eye tracking setup, according to an important aspect of the present disclosure, a more unobtrusive device design and a more robust cross-user gaze detection is thus enabled (for example a mean angular prediction error lower than 2°).

The exact internal architecture of the network, i.e. the exact number, dimensions and sequence of convolutional and other layers has been found not to be very critical for the systems to work sufficiently well.

However, the network should preferably be highly efficient in order to allow for real-time interaction and embedded computation. Similarly, the precise individual values of the parameters which result from the training process influence the final accuracy of the trained network only to a small degree.

In particular network architectures optimized for small size or execution on mobile or embedded platforms have been found to be suitable. Candidates using CNNs thus include but are not limited to LeNet, SqueezeNet, MobileNet, Darknet, Resnet18 and any adaptations of these. Such network architectures are generally known and therefore need not be further described here in detail.

In a preferred embodiment, the neural network additionally uses one or more so-called "squeeze-and-excitation" (SE) blocks (layers). Such blocks perform feature recalibration. Input data or features U (W×H×C corresponding to image width×image height×number of channels) are first passed through a squeeze operation, which aggregates the feature maps across spatial dimensions W×H to produce a channel descriptor (1×1×C). This descriptor embeds the global distribution of channel-wise feature responses, enabling information from the global receptive field of the network to be leveraged by its lower layers. This is followed by an excitation operation, in which sample-specific activations, learned for each channel by a self-gating mechanism based on channel dependence, govern the excitation of each channel. The feature maps U are then reweighted channel-wise by these additionally learned parameters to generate the output of the SE block which can then be fed directly into subsequent layers.

Once, a core data corpus has been created and a CNN has been trained using the database DB (and the methods herein described), the parameters {tCNN} of the trained convolutional neural network tCNN can be uploaded to the memory of the head-wearable device 720.

FIG. 6 shows an exemplary flow of gaze direction prediction. The cameras of the device 720 record a live video stream of eye images, which are provided as an input data stream to the (integrated) processing unit 725, which uses a CNN-module 7251 to apply the trained network tCNN to the images (forward pass the images through the network tCNN) and thus calculates the predicted gaze direction $g_{pr}$. The optional scene camera can simultaneously record a video stream of images corresponding to part of the FOV of the user wearing the device 720. This video stream can be output by the device 720 together with the predicted gaze direction $g_{pr}$, or the gaze direction $g_{pr}$ can be output alone, via any of the device's data interfaces, or can be stored in the device memory. Thus, a compact, wearable and fully embedded device 720 for end-to-end gaze estimation results, which allows for accurate real-time inference of gaze direction directly on the device, by using a pre-trained and optimized neural network model.

The simplest possible use scenario is thus that a user receives the device 720, puts it on and can start tracking without any further setup steps. The results could for example be relayed to and visualized in real-time on a local or remote device, such as a mobile phone, tablet, laptop, or any kind of visualization device. Visualization in the simplest case consists of displaying the video stream of the scene camera with the predicted gaze point indicated.

In a further embodiment, a calibration (left in FIG. 6, see also FIG. 3B) and correction method (block 7252) as described herein may be performed for the user. It is to be understood, that a calibration step is optional, since the use of a trained CNN enables the wearable device 720 to work with sufficient accuracy in a calibration-free mode. However, performing an optional calibration method is able to produce further beneficial effects.

Firstly, such procedure can provide a simple user-specific correction function $F_{corr}$ which can be applied on-the-fly to the predicted gaze $g_{pr}$ which is output by the network tCNN, in order to further and instantaneously improve the accuracy achieved for that specific user. One possible example of correction functions are simple bivariate polynomials of adjustable degree. This correction could for example be applied either only during the present use session, or saved and applied also during subsequent use session of that user. The rationale behind such a procedure is that due to the physiology of the human eye, a universal network may hardly achieve 100% accuracy. For example, there exists a person-specific angle between the optical axis of each eye and the actual visual axis or line of sight of that eye. This angle is usually different in the left and right eye of a person, varies over the population and is per se unknown. In other words, a trained NN averages over this variation. Accordingly, a person-specific calibration is able to further increase the accuracy with respect to the predictions.

Secondly, datasets from one or more calibration methods performed by individual users can be used in conjunction with the existing core data corpus in various ways to improve the accuracy of the predictions.

For example, labelled calibration data from a specific user can be used to fine-tune the universal network into a personal network which then performs more accurate predictions for that specific user. This can for example be done by re-training or re-optimizing only parts of the neural network, i.e. only a subset of the entire parameters of the universal network, to better reproduce the ground truth of that specific user.

Thirdly, labelled calibration datasets from a plurality of different users can be added to the core data corpus itself over time (see the dashed-dotted arrow in FIG. 5) as more users use the devices 720 and perform calibration methods. The core data corpus can thus dynamically grow in volume, and the universal network can at intervals be refined respectively re-trained to provide an even more accurate universal neural network. This can be done from scratch using the increased training data volume, but with all model parameters re-initialized, or a re-training of the universal NN can use all of or part of the previous version of the parameters as initialization.

Thus, a threefold added benefit results: the calibration method can instantaneously improve the accuracy for a specific user by generating a correction function $F_{corr}$ to be applied to the prediction of the universal NN, one or more such procedures can also turn the universal NN into a more accurate personal model, and calibration methods performed by one or many users can even serve to improve the database DB and thus the universal NN, from which all users benefit immediately globally.

In an exemplary embodiment, the calibration method includes instructing a user wearing the device 720 to look at a particular known marker point, pattern or object in space, whose coordinates within the video images recorded by a scene camera connected to or provided by the device 720 can be precisely determined in an automated way by state of the art machine learning, computer vision or image processing techniques (block 7253 in FIG. 6). The image or images recorded by the cameras facing the eye(s) of the user are used to predict the user's gaze direction (gaze point) in block 7251. The offset of the predicted gaze direction (gaze point) $g_{pr}$ and the expected gaze direction (gaze point) $g_e$ defined by the marker position can then be calculated and used to generate a correction mapping or function $F_{corr}$ in a block 7254 to be applied henceforth (block 7252) to the prediction of the universal NN to arrive at a calibrated gaze-value $g_{cpr}$.

Alternatively to such an explicit calibration method, an implicit calibration method, like for example based on point-of-regard priors (e.g. mouse cursor on a computer screen) or saliency maps could be employed.

Possible use scenarios involving calibration are thus as follows.

At the first time a new user uses the device 720, the user can be given the possibility to perform a calibration, the result of which is used in all subsequent use sessions (once in a lifetime calibration). Alternatively, the user can be given the possibility to perform a calibration at the beginning of each new use session or at given time intervals, like e.g. on a daily basis.

Alternatively, the users can themselves invoke the calibration at their own volition. Furthermore, every time a user performs a calibration, the corresponding calibration datasets can be automatically sent to computing system 710 (when connected the next time). Accordingly, the computing system 710 can perform one of the refinement methods (updating the database DB, retraining the network tCNN) as described herein. This may be achieved in an anonymized way, since only the eye images and ground truth coordinates need to be transmitted.

The described calibration methods yield pairs of images labeled with the ground truth gaze location, which can be used to improve the universal NN as described above.

However, besides those labeled images it is optionally possible also to collect and store images in datasets obtained during everyday use. These datasets cannot be labelled with the ground truth gaze location, as this information is not available outside of calibration mode. However, a big corpus of unlabeled data still yields information about the contained image diversity. Techniques from the fields of unsupervised and semi-supervised learning can be utilized to source this information in order to improve the universal model or a person-specific model similarly to how it is described above.

To make it easier for a new user of the device 720 to use their person-specific model for gaze estimation along with other hyper parameters that might be set in their profile, it is possible to utilize automatic user identification and load the user's profile without them having to actively select it.

The user identification can be based on a separate learning-based algorithm. As training data for this algorithm one can use the available training data from all known users of a particular instance of a wearable device collected through either calibrations or during everyday use.

Since the number of regular users of one specific instance of a wearable device 720 is small, for example below 50, a simple off-the-shelf learning algorithm like a Support-Vector-Machine or a Random Forest is enough to train the user identifier.

Further, identifying the user also allows detecting a) new users that have not been calibrated before and b) when the current user has calibrated last. In both cases the user can then choose to perform a calibration, respectively the device can propose a calibration to the identified user.

The device can also be embodied in configurations other than in the form of spectacles, such as for example as integrated in the nose piece or frame assembly of an AR or VR head-mounted display (HMD) or goggles or similar device, or as a separate nose clip add-on or module for use with such devices. In this case the optical sensor feed could go into a multi-purpose computer vision processing chip that handles the CNN computation for gaze estimation alongside other tasks related to the AR/VR experience. This could also be a dedicated chip that does only (CNN-based) gaze estimation but the chip lives on and is powered by a PCB that hosts other HMD components as well. The system can thus also include a display device or screen for presenting information to the user. The methods described herein are applicable without adaptation to such an alternative device and/or system According to an embodiment, a system for improving the prediction of gaze-related parameters includes at least one head-mountable device and a computing system connectable with the at least one head-mountable device and configured to host a database. The at least one head-mountable device includes a first camera for generating a left image of at least portion of a left eye of a user and a second camera to generate a right image of at least portion of a right eye of the user when the user is wearing the head-mountable device. The computing system and the at least one head-mountable device are configured to upload datasets from the at least one head-mountable device to the first database and to download parameters of a neural network, in particular parameters of a convolutional neural network from the computing system to the at least one head-mountable device. The datasets includes a respective left image, a respective right image and a respective representation of a gaze-related parameter. The computing system is typically further configured to use the database for training the neural network and/or to determine the parameters of the neural network.

Although various exemplary embodiments of the invention have been disclosed, it will be apparent to those skilled in the art that various changes and modifications can be made which will achieve some of the advantages of the invention without departing from the spirit and scope of the invention. It will be obvious to those reasonably skilled in the art that other components performing the same functions may be suitably substituted. It should be mentioned that features explained with reference to a specific figure may be combined with features of other figures, even in those cases in which this has not explicitly been mentioned. Such modifications to the inventive concept are intended to be covered by the appended claims.

While processes may be depicted in the figures in a particular order, this should not be understood as requiring, if not stated otherwise, that such operations have to be performed in the particular order shown or in sequential order to achieve the desirable results. In certain circumstances, multitasking and/or parallel processing may be advantageous.

Spatially relative terms such as "under", "below", "lower", "over", "upper" and the like are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

REFERENCE NUMBERS 1 spectacles device
2 spectacles body
3 nose bridge portion
4 frame
5 illumination means
6 scene camera
7 processing unit
10 left side
11 left ocular opening
12 left lateral portion
13 left holder
14 left camera
15 optical axis (left camera)
16
17 left inner eye camera placement zone
18 left outer eye camera placement zone
19 left eye
20 right side
21 right ocular opening
22 right lateral portion
23 right holder
24 right camera
25 optical axis (right camera)
26
27 right inner eye camera placement zone
28 left outer eye camera placement zone
29 right eye
30 bounding cuboid
31 left lateral surface
32 right lateral surface
33 upper surface
34 lower surface
100 middle plane
101 horizontal direction
102 vertical direction
103 down
104 up
105 front
106 back
α angle of inner left camera 14
β angle of inner right camera 24
γ angle of outer left camera 24
δ angle of outer right camera 24
500-502 system
510 computing system/server
520, 530 head-wearable spectacles device
525, 535 processing unit
>=1000 methods, method steps

The invention claimed is:

1. A method for detecting one or more gaze-related parameters of a user, the method comprising:
creating a left image of at least a portion of a left eye of the user using a first camera of a head-wearable device worn by the user;
creating a right image of at least a portion of a right eye of the user using a second camera of the head-wearable device;
concatenating the left image and the right image to form a concatenated image;
feeding the concatenated image as an input into a convolutional neural network; and
obtaining the one or more gaze-related parameters from the convolutional neural network as a result of the concatenated image input.

2. The method according to claim 1, wherein the one or more gaze-related parameters are selected from a list consisting of: a gaze direction, a cyclopian gaze direction, a 3D gaze point, a 2D gaze point, a visual axis orientation, an optical axis orientation, a pupil axis orientation, a line of sight orientation, an orientation and/or a position and/or an eyelid closure, a pupil area, a pupil size, a pupil diameter, a sclera characteristic, an iris diameter, a characteristic of a blood vessel, a cornea characteristic of at least one eye, a cornea radius, an eyeball radius, a distance pupil-center to cornea-center, a distance cornea-center to eyeball-center, a distance pupil-center to limbus center, a cornea keratometric index of refraction, a cornea index of refraction, a vitreous humor index of refraction, a distance crystalline lens to eyeball-center, to cornea center and/or to corneal apex, a crystalline lens index of refraction, a degree of astigmatism, an orientation angle of a flat and/or a steep axis, a limbus major and/or minor axes orientation, an eye cyclo-torsion, an eye intra-ocular distance, an eye vergence, a statistics over eye adduction and/or eye abduction, and a statistics over eye elevation and/or eye depression, data about blink events, drowsiness and/or awareness of the user, parameters for user iris verification and/or identification.

3. The method according to claim 1, comprising locating the first and second cameras within a range of 32 to 40 degrees with respect to the median plane of the head-wearable device.

4. The method according to claim 1, comprising locating the first and second cameras within a range of 114 to 122 degrees with respect to the median plane of the head-wearable device.

5. The method according to claim 1, wherein the first and second images are not preprocessed to obtain spatial and/or temporal patterns or arrangements prior to feeding them as concatenated image to the convolutional neural network.

6. The method according to claim 1, wherein the left and right images do not undergo feature extraction prior to feeding them as concatenated image to the convolutional neural network.

7. The method according to claim 1, wherein an output of the convolutional neural network is not postprocessed for obtaining the one or more gaze-related parameter.

8. The method according to claim 1, wherein the convolutional neural network comprises at least 6 layers.

9. The method according to claim 8, wherein the convolutional neural network comprises between 12 and 30 layers.

10. The method according to claim 1, wherein the convolutional neural network comprises a two-dimensional input layer.

11. The method according to claim 10, wherein the input layer is a N×2N matrix.

12. The method according to claim 11, wherein N is smaller or equal than 50.

13. The method according to claim 1, wherein the convolutional neural network has a filter kernel of size M with M being in the range from 2 to 6.

14. The method according to claim 1, wherein the one or more gaze-related parameters are selected from a list comprising a 3D gaze point and a 2D gaze point.

15. The method according to claim 1, wherein the one or more gaze-related parameters are obtained from the convolutional neural network as the result of only inputting the concatenated image.

16. A non-transitory computer-readable medium comprising instructions which, when executed on a computer, cause the computer to carry out the steps of:
creating a left image of at least a portion of a left eye of the user using a first camera of a head-wearable device worn by the user;
creating a right image of at least a portion of a right eye of the user using a second camera of the head-wearable device;
concatenating the left image and the right image to form a concatenated image;
feeding the concatenated image as an input into a convolutional neural network; and
obtaining the one or more gaze-related parameters from the convolutional neural network as a result of the concatenated image input.

17. A system comprising:
a device comprising a left camera for taking a left image of at least a portion of a left eye of a user wearing the device, and a right camera for taking a right image of at least a portion of a right eye of the user wearing the device; and
a processing unit configured to receive the left image, receive the right image, concatenate the left image and the right image to form a concatenated image, feed the concatenated image as an input into a trained convolutional neural network, and obtain one or more gaze-related parameters from the trained convolutional neural network as a result of the concatenated image input.

18. The system according to claim 17, wherein the device is a wearable device, and wherein the processing unit is integrated in the wearable device.

19. The system according to claim 18, wherein the wearable device is a head-wearable device.

20. The system according to claim 17, wherein the processing unit is integrated into a desktop computer, a server, a smart phone, a tablet, or a laptop.

* * * * *